(12) United States Patent
Taniguchi et al.

(10) Patent No.: US 8,367,050 B2
(45) Date of Patent: Feb. 5, 2013

(54) PHOTOCATALYTIC MATERIAL AND PHOTOCATALYTIC MEMBER AND PURIFICATION DEVICE USING THE PHOTOCATALYTIC MATERIAL

(75) Inventors: Noboru Taniguchi, Osaka (JP); Tomohiro Kuroha, Osaka (JP); Shuzo Tokumitsu, Hyogo (JP); Kenichi Tokuhiro, Osaka (JP)

(73) Assignee: Panasonic Corporation, Osaka (JP)

( * ) Notice: Subject to any disclaimer, the term of this patent is extended or adjusted under 35 U.S.C. 154(b) by 574 days.

(21) Appl. No.: 12/596,350

(22) PCT Filed: Apr. 18, 2008

(86) PCT No.: PCT/JP2008/001020
§ 371 (c)(1),
(2), (4) Date: Oct. 16, 2009

(87) PCT Pub. No.: WO2008/132823
PCT Pub. Date: Nov. 6, 2008

(65) Prior Publication Data
US 2010/0135864 A1     Jun. 3, 2010

(30) Foreign Application Priority Data

Apr. 18, 2007  (JP) ................. 2007-109790
Apr. 18, 2007  (JP) ................. 2007-109791
Oct. 1, 2007   (JP) ................. 2007-257939
Oct. 1, 2007   (JP) ................. 2007-257940

(51) Int. Cl.
*A61L 9/01*   (2006.01)
*A61K 7/18*   (2006.01)
*C04B 35/00*  (2006.01)
*B32B 5/16*   (2006.01)
*B01J 31/00*  (2006.01)

(52) U.S. Cl. .......... 424/76.2; 424/76.8; 424/52; 96/224; 96/55; 252/62.3; 252/600; 524/80; 524/497; 428/323; 428/329; 502/150; 502/171

(58) Field of Classification Search ................ 422/5, 24, 422/186.3, 306, 184.04; 424/76.2, 76.8, 424/52; 96/224, 55; 252/62.3, 600; 524/80, 524/497; 428/323, 329; 502/150, 171
See application file for complete search history.

(56) References Cited

U.S. PATENT DOCUMENTS 5,759,948 A      6/1998  Takaoka et al.
6,281,277 B1 *   8/2001  Ishii et al. ............... 524/444
(Continued)

FOREIGN PATENT DOCUMENTS

JP   1-218635    8/1989
JP   7-303835   11/1995
(Continued)

OTHER PUBLICATIONS

Heller, et al., "Controlled Suppression or Enhancement of the Photoactivity of Titanium Dioxide (Rutile) Pigment", Proceedings Electrochemical Society, 1988, vol. 88, No. 14, pp. 23-33.

(Continued)

*Primary Examiner* — Jill Warden
*Assistant Examiner* — Monzer Chorbaji
(74) *Attorney, Agent, or Firm* — Hamre, Schumann, Mueller & Larson, P.C.

(57) ABSTRACT

Provided are a photocatalytic material that improves a decomposition performance and a decomposition rate, as well as a photocatalytic member and a purification device in which the photocatalytic material is used. The photocatalytic member is a photocatalytic member (1) that includes a substrate (10) and a photocatalyst layer (11) formed on a surface of the substrate (10), wherein the photocatalyst layer (11) contains a titanium oxide photocatalyst and zeolite, the titanium oxide photocatalyst containing at least an anatase-type titanium oxide and fluorine, in which a content of the fluorine in the titanium oxide photocatalyst is 2.5 wt % to 3.5 wt %, and 90 wt % or more of the fluorine is chemically bonded to the anatase-type titanium oxide.

11 Claims, 8 Drawing Sheets

U.S. PATENT DOCUMENTS

| | | | |
|---|---|---|---|
| 6,376,057 B1 * | 4/2002 | Akao et al. | 428/215 |
| 6,533,966 B1 * | 3/2003 | Nonninger et al. | 252/520.1 |
| 6,890,645 B2 * | 5/2005 | Disse et al. | 428/323 |
| 7,521,391 B2 | 4/2009 | Sakatani et al. | |
| 7,521,394 B2 | 4/2009 | Xie et al. | |
| 7,771,688 B2 | 8/2010 | Lee et al. | |
| 8,148,289 B2 | 4/2012 | Taniguchi et al. | |
| 2004/0118285 A1 * | 6/2004 | Kim et al. | 96/55 |
| 2004/0170578 A1 * | 9/2004 | Sugihara | 424/52 |
| 2005/0020440 A1 | 1/2005 | Domen et al. | |
| 2005/0233893 A1 * | 10/2005 | Sakatani et al. | 502/150 |
| 2006/0210798 A1 | 9/2006 | Burda | |
| 2010/0111817 A1 | 5/2010 | Taniguchi et al. | |
| 2012/0157300 A1 | 6/2012 | Taniguchi et al. | |

FOREIGN PATENT DOCUMENTS

| | | |
|---|---|---|
| JP | 11-188703 | 7/1999 |
| JP | 11-319570 | 11/1999 |
| JP | 2000-107610 | 4/2000 |
| JP | 2002-136811 | 5/2002 |
| JP | 2003-236389 | 8/2003 |
| JP | 2004-292225 | 10/2004 |

OTHER PUBLICATIONS

Wang, et al., "Wide-Range Tuning of the Titanium Dioxide Flat-Band Potential by Adsorption of Fluoride and Hydrofluoric Acid", J. Phys. Chem., 1990, vol. 94, pp. 4276-4280.

Janczyk, et al., "Singlet Oxygen Photogeneration at Surface Modified Titanium Dioide", J. Am. Chem. Soc., 2006, vol. 128, No. 49, pp. 15574-15575.

Ayllon, et al., "Preparation of anatase powders from fluorine-complexed titanium(iv) aqueous solution using microwave irradiation", Journal of Materials Chemistry, vol. 10, 2000, pp. 1911-1914.

Li, et al., "Fluorine-doped $TiO_2$ powders prepared by spray pyrolysis and their improved photocatalytic activity for decomposition of gas-phase acetaldehyde", Journal of Fluorine Chemistry, vol. 26, 2005, pp. 69-77.

Xu, et al., "Synthesis of fluorine-doped titania-coated activated carbon under low temperature with high photocatalytic activity under visible light", Journal of Physics and Chemistry of Solids, vol. 69, 2008, pp. 2366-2370.

* cited by examiner

PHOTOCATALYTIC MATERIAL AND PHOTOCATALYTIC MEMBER AND PURIFICATION DEVICE USING THE PHOTOCATALYTIC MATERIAL

TECHNICAL FIELD

The present invention relates to a photocatalytic material containing titanium oxide, as well as a photocatalytic member and a purification device using the photocatalytic material.

BACKGROUND ART

Recently, titanium oxide photocatalysts have been put into practical use in various situations, for the purposes of sterilization, antifouling, and the like. The use of the same now is not limited to outdoor use, but is spreading to indoor use for the purposes of sterilization, deodorization, and the like. Because of this, a titanium oxide has been demanded that can be excited efficiently even by an energy in a visible region in a titanium oxide excitation system that conventionally has required an energy in an ultraviolet region. Such demand often is met by a titanium oxide supporting a foreign element or forming a solid solution with a foreign element. A wavelength for exciting the titanium oxide can be controlled depending on the type of a foreign element to be added.

However, in many cases, such a treatment that causes titanium oxide to support a foreign element or causes titanium oxide to form a solid solution with a foreign element significantly reduces an efficiency of excitation inherent to the titanium oxide. In return for the excitability with respect to visible light, an effect to be achieved originally by ultraviolet rays is reduced, which results in a decrease in activity in many cases.

Conventionally, it is known that the photocatalytic activity of titanium oxide is enhanced by elimination of lattice defects in titanium oxide using a mineral acid or the like (Non-Patent Document 1). Especially, it is known that a hydroxyl group on a surface of titanium oxide can be replaced easily with fluorine. Therefore, there have been proposals to treat titanium oxide with a fluorine compound such as hydrofluoric acid so as to enhance the photocatalytic performance in the titanium oxide excitation system using ultraviolet rays (Non-Patent Document 2, Patent Documents 1 and 2). However, some types of titanium oxide treated as above did not fully exhibit the effect.

On the other hand, regarding deodorization and purification of air, a technology that is capable of promptly deodorizing and decomposing four major odorous components—acetaldehyde, acetic acid, ammonia and sulfur compound gas (e.g. hydrogen sulfide and methyl mercaptan)—has been demanded. Exemplary methods of the above technology are as follows: a method of concentrating and storing odor using an adsorbent such as activated carbon or zeolite; and a method of directly decomposing odor by thermal decomposition, thermal catalytic decomposition, ozone decomposition, plasma discharge decomposition, photocatalyst decomposition, or the like.
[Patent Document 1] JP 07-303835 A
[Patent Document 2] JP 2004-292225 A
[Non-Patent Document 1] Proceedings Electrochemical Society 1988, vol. 88, no. 14, pp. 23-33
[Non-Patent Document 2] The Journal of Physical Chemistry, 1990, vol. 94, pp. 4276-4280

DISCLOSURE OF INVENTION

Problem to be Solved by the Invention

However, the method using an adsorbent only provides poor adsorbability with respect to acetaldehyde, which is highly contained in mainstream smoke and secondary smoke of tobacco products, and therefore has a problem that odor once adsorbed is again released. Moreover, the direct decomposition method using thermal decomposition or catalytic decomposition has problems in heat generation and power consumption; ozone decomposition and plasma discharge decomposition have a problem in safety because of ozone generation; and photocatalyst decomposition has a problem in the decomposition rate. Especially, in photocatalyst decomposition, as compared with the other methods, a superior ability of eliminating acetaldehyde is exhibited owing to the gas adsorbability originally possessed by titanium oxide used as a photocatalyst material, but the decomposition rate is insufficient for practical use.

Therefore, the present invention provides a photocatalytic material containing titanium oxide that is capable of improving a decomposition performance and a decomposition rate, as well as a photocatalytic member and a purification device using the photocatalytic material.

Means for Solving Problem

A photocatalytic material of the present invention includes a titanium oxide photocatalyst and zeolite, the titanium oxide photocatalyst containing at least an anatase-type titanium oxide and fluorine,
wherein a content of the fluorine in the titanium oxide photocatalyst is 2.5 wt % to 3.5 wt %, and
90 wt % or more of the fluorine is chemically bonded to the anatase-type titanium oxide.

A photocatalytic member of the present invention is a photocatalytic member comprising a substrate, and a photocatalyst layer formed on a surface of the substrate,
wherein the photocatalyst layer contains the above-described photocatalytic material of the present invention.

A purification device of the present invention comprises the above-described photocatalytic member of the present invention, and a light source that irradiates the photocatalytic member with light having a wavelength of 400 nm or less.

Effects of the Invention

The photocatalytic material, the photocatalytic member, and the purification device of the present invention include a titanium oxide photocatalyst having high photocatalytic activity and zeolite. Therefore, it is possible to improve, for example, an odorous component decomposition performance, and an odorous component decomposition rate.

Figure 1:
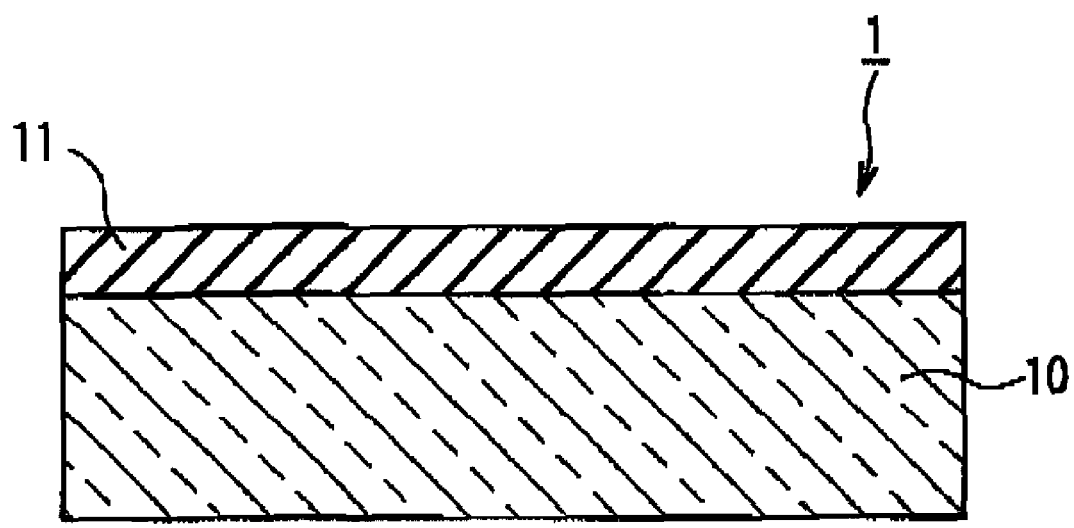
FIG. 1 is a cross-sectional view of a photocatalytic member according to Embodiment 1 of the present invention.

EXPLANATION OF REFERENCE CODES 1, 21, 31, 41, 51, 61, 71, 101 photocatalytic member
2 co-flow air purification device
201 cross-flow air purification device
3 to 5 air purification device
6, 8 liquid purification device
10, 20, 21a, 31a, 41a, 51a, 61a substrate
11, 21b, 31b, 4113, 51b, 61b, 71b photocatalyst layer
20, 25, 30, 40, 50, 60, 70 container
22, 32 light source
23, 52 blowing means
25a parting plate
33 reflection plate
42 oil mist
52 blowing means
53 prefilter
62a liquid-feeding valve
62b liquid-discharging valve
63 contaminated water
71a glass substrate
72 black light
80 Petri dish
81 stand

DESCRIPTION OF PREFERRED EMBODIMENTS

A photocatalytic material of the present invention is a photocatalytic material containing a titanium oxide photocatalyst and zeolite, the titanium oxide photocatalyst containing at least an anatase-type titanium oxide (hereinafter also referred to as "titanium oxide" simply) and fluorine, wherein a content of the fluorine in the titanium oxide photocatalyst is 2.5 wt % to 3.5 wt %, and 90 wt % or more of the fluorine is chemically bonded to the above anatase-type titanium oxide. With the photocatalytic material of the present invention, the performance of decomposing organic molecules (e.g. odorous components) can be improved, with an adsorbing function of zeolite. Further, since it contains the titanium oxide photocatalyst, the photocatalytic activity can be improved. Therefore, an odorous component decomposition rate, for example, can be improved.

In the photocatalytic material of the present invention, for example, from the viewpoint of maintaining the photocatalytic activity and the deodorizing power, zeolite mentioned above preferably contains at least one of a mordenite-form zeolite and a ZSM-5-form zeolite.

In the photocatalytic material of the present invention, for example, from the viewpoint of maintaining the photocatalytic activity and the deodorizing power, zeolite mentioned above preferably contains silica and alumina, and a molar component ratio between silica and alumina (silica/alumina) in the zeolite preferably is 240 or more.

In the present invention, a photocatalyst refers to a substance that shows catalytic activity when irradiated with light such as ultraviolet rays, and preferably, to a substance that, when irradiated with light, can decompose and eliminate various organic and inorganic compounds and perform sterilization. The titanium oxide photocatalyst of the present invention preferably can be used for, for example, decomposing and eliminating odorous components such as acetaldehyde and methyl mercaptans; sterilizing and eliminating fungi and algae; oxidatively decomposing and eliminating nitrogen oxides; and imparting an anti-fouling function by causing glass to have ultra-hydrophilic properties.

In the present invention, examples tithe photocatalytic activity include a function of decomposing organic compounds oxidatively when the titanium oxide photocatalyst is irradiated with ultraviolet rays. The photocatalytic activity of the present invention can be evaluated by, for example, a carbon dioxide generation rate that indicate a rate at which carbon dioxide is generated along with the oxidation of organic compounds when the organic compounds in a gaseous or liquid state and the titanium oxide photocatalyst coexist and are irradiated with ultraviolet rays of 400 nm or less. Preferably, the photocatalytic activity can be evaluated by, for example, a carbon dioxide generation rate at which carbon dioxide is generated by the oxidative decomposition of acetaldehyde. The reaction is expressed by a reaction formula (I) shown below

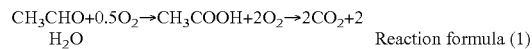

$$CH_3CHO+0.5O_2 \rightarrow CH_3COOH+2O_2 \rightarrow 2CO_2+2H_2O \quad \text{Reaction formula (1)}$$

The titanium oxide photocatalyst used in the present invention contains fluorine in the range of 2.5 wt % to 3.5 wt % in element content; more preferably, in the range of 2.7 wt % to 3.3 wt %; and further preferably, in the range of 2.9 wt % to 3.1 wt %. Setting the content of fluorine to 2.5 wt % or more makes it possible to improve the photocatalytic activity while setting the content of fluorine to 3.5 wt % or less makes it possible to suppress a decline in the photocatalytic activity.

The reason why the above-titanium oxide photocatalyst improves the photocatalytic activity is uncertain, but it is assumed as follows: by the setting of the content of fluorine at 2.5 wt % or more, the fluorine, which has a large electronegativity, comes to stay on a surface of the titanium oxide. Owing to the electron-withdrawing function of the fluorine located on the surface of the titanium oxide, for example, a hydroxyl group located adjacent thereto is activated, whereby a hydroxyl radical tends to be generated. As a result, the photocatalytic reaction can be accelerated. Although the photocatalytic reaction can develop even when the content of fluorine is 2.5 wt % or less, the effect of accelerating the photocatalytic reaction can be enhanced greatly when the content of fluorine is 2.5 wt % or more.

Further, the reason why the above-titanium oxide photocatalyst can suppress a decline in the photocatalytic activity is uncertain, but it is assumed as follows: by setting the content of fluorine at 3.5 wt % or less, for example, the amount of fluorine covering the surface of the titanium oxide can be kept in an adequate range, whereby the number of hydroxyl groups required for the photocatalytic reaction can be ensured.

Furthermore, in the titanium oxide photocatalyst used in the present invention, 90 wt % or more of fluorine is chemically bonded to the titanium oxide. This allows the fluorine to exhibit its own electron-withdrawing function effectively, whereby the photocatalytic reaction accelerating effect can be enhanced. Specifically, the above chemical bond preferably is anionic bond because in such a case fluorine and titanium oxide are bonded to each other firmly and the photocatalytic reaction accelerating effect is enhanced further. It should be noted that the ionic bond of fluorine and titanium oxide can be determined in a measurement using a photoelectron spectroscopic analyzer, which is described later.

In the above-described titanium oxide photocatalyst, from the viewpoint of accelerating the photocatalytic reaction, a proportion of fluorine chemically bonded to the titanium oxide is 90 wt % or more of the entirety of the fluorine in the titanium oxide photocatalyst preferably 95 wt % or more; and more preferably 100 wt %, that is, the entirety of the fluorine contained in the titanium oxide photocatalyst is chemically bonded to the titanium oxide. In the titanium oxide photocatalyst of the present invention, the content of fluorine chemically bonded to titanium oxide is, for example, 2.35 wt % to 3.5 wt %; preferably 2.5 wt % to 3.5 wt %; and more preferably 2.5 wt % to 3.3 wt %.

In the present invention, a chemical bond between titanium oxide and fluorine refers to a state in which titanium oxide and fluorine are chemically bonded to each other, and preferably, to a state in which titanium oxide and fluorine are, not supported or mixed, but bonded to each other at the atomic level. In the present invention, chemically-bonded fluorine refers to, tithe fluorine contained in the titanium oxide photocatalyst, the fluorine that is not eluted into water, for example. The amount of such fluorine chemically bonded to the titanium oxide can be measured by the following method: first, a titanium oxide photocatalyst is dispersed into water; then the dispersion solution is kept at pH=3 or less, or pH=10 or more with a pH adjuster (e.g. hydrochloric add, ammonia water); the amount of fluorine ion eluted into water is measured by a colorimetric titration, or the like; and the above eluted amount is subtracted from the total amount of the fluorine contained in the titanium oxide photocatalyst. Thus, the amount of the fluorine chemically bonded to the titanium oxide can be determined. The amount of fluorine ion eluted into water can be measured as in Examples described later.

In the above-described titanium oxide photocatalyst, it is preferable that at least a part of the fluorine chemically bonded to the titanium oxide is located on surfaces of titanium oxide. Because the photocatalytic reaction mainly occurs on surfaces of titanium oxide, if the fluorine is located on surfaces of titanium oxide, the photocatalytic reaction accelerating effect is enhanced further. It should be noted that the amount of fluorine chemically bonded to the titanium oxide on surfaces of the titanium oxide can be determined in a measurement using a photoelectron spectroscopic analyzer, as in Examples described later.

In the present specification, "titanium oxide and fluorine are bonded ionically" refers to a case in which, when the titanium oxide photocatalyst is analyzed by a photoelectron spectroscopic analyzer, the catalyst shows a spectrum such that a peak-top of 1s orbital of fluorine ($F_{1s}$) appears in a range from 683 eV to 686 eV. This is ascribed to titanium fluoride, which results from ionic bonding of fluorine and titanium, having a peak-top value falling in the above range.

In the case where the above-described titanium oxide photocatalyst includes sodium, and where a content of sodium in the entirety of the titanium oxide photocatalyst is assumed to be A wt % and a content of fluorine in the entirety of the titanium oxide photocatalyst is assumed to be B wt %, a ratio A/B is preferably 0.01 or less; more preferably 0.005 or less; and further preferably 0.001 or less. If the ratio A/B is 0.01 or less, a decline in the photocatalytic activity can be suppressed. The reason is uncertain, yet it is assumed that, for example, a decrease in the amount of sodium with respect to fluorine causes the decline in the photocatalytic activity due to the reaction between sodium and fluorine to be suppressed. It should be noted that it is most preferable that the content of sodium is 0, that is, it is most preferable that the ratio A/B is 0. Regarding impurities other than sodium also, it is preferable that there are less impurities; and it is most preferable that there are no impurities. Examples of an element that can be impurities include potassium, aluminum, and transition metals.

Regarding the titanium oxide photocatalyst used in the present invention, a specific surface area thereof is preferably in a range of 200 m$^2$/g to 350 m$^2$/g; and more preferably, in a range of 250 m$^2$/g to 350 m$^2$/g. Here, in the present invention, the specific surface area refers to a value of a surface area per 1 g of the titanium oxide photocatalyst in powder form measured by a BET method (nitrogen adsorption-desorption method). When the specific surface area is 200 m$^2$/g or more, the area in contact with an object to be decomposed can be large. Further, in the case where an anatase-type titanium oxide is used, and if the specific surface area thereof is 350 m$^2$/g or less, a photocatalytic reaction with higher efficiency can be achieved compared to the case where an amorphous titanium oxide is used. Here, the anatase-type titanium oxide refers to a titanium oxide showing a diffraction peak at a diffraction angle 2θ=25.5 degrees in a measurement with a powder X-ray diffractometer using copper electrodes as working electrodes.

The titanium oxide photocatalyst used in the present invention can be produced through, for example, the following producing method. First, a pH of an aqueous dispersion solution of titanium oxide is adjusted with an alkaline solution until the pH thereof becomes in a range of 7.5 to 9.5, and thereafter the solution is filtered. Subsequently, the filtration residue obtained by the filtration is re-dispersed into water. Then, a fluorine compound is added to the re-dispersion solution obtained by the re-dispersion so that a suspension is obtained, and thereafter, a pH of the suspension is adjusted with an acid until the pH thereof becomes 3 or less, whereby the titanium oxide and the fluorine compound are caused to react with each other. Then, the reaction product obtained by the reaction is washed. With the present method, the above-described titanium oxide photocatalyst can be produced easily. In this method, if the amount of added fluorine compound is increased, the titanium oxide dissolves itself. Therefore, the content of fluorine in the titanium oxide photocatalyst can be controlled easily to 3.5 wt % or lower. Further, in the case where the reaction product is washed with water, the water washing preferably is carried out until an electric conductivity of water used in the washing becomes 1 mS/cm or less, as an index for washing. The water used for washing in the present invention refers to, for example, water that is used for washing a reaction product and thereafter is collected. The electric conductivity can be measured in a manner as in Examples to be described later.

In the present method, the aforementioned re-dispersion solution contains an anatase-type titanium oxide having such a surface acidity that an amount of adsorbed n-butylamine per 1 gram of the titanium oxide is, for example, 8 μmol or less. Thus, using as a starting material the anatase-type titanium oxide having a surface that is almost basic, a titanium oxide photocatalyst can be prepared that contains fluorine in a range of 2.5 wt % to 3.5 wt % as an element. Therefore, in the foregoing producing method, the steps of "adjusting a pH of an aqueous dispersion solution of a titanium oxide with an alkaline solution until the pH thereof becomes in a range of 7.5 to 9.5, and thereafter filtering the solution" and "re-dispersing the filtration residue obtained by the filtration into water" may not be used, but instead, an aqueous dispersion solution of an anatase-type titanium oxide that adsorbs n-butylamine in an amount of 8 μmol/g or less may be used.

Therefore, the titanium oxide photocatalyst containing fluorine can be produced through the following steps: mixing a fluorine compound and an aqueous dispersion solution of an anatase-type titanium oxide that adsorbs n-butylamine in an amount of 8 μmol/g or less whereby a mixed solution containing titanium oxide and fluorine and having a pH of 3 or less is prepared, so that the titanium oxide and the fluorine compound are caused to react with each other; and washing the reaction product obtained.

As the anatase-type titanium oxide that adsorbs n-butylamine in an amount of 8 μmol/g or less, for example, SSP-25 manufactured by SAKAI Chemical Industry Co., Ltd. can be used. As the aqueous dispersion solution of the same, for example, CSB-M manufactured by SAKAI Chemical Industry Co., Ltd. can be used.

Here, the method for measuring the amount of adsorbed n-butylamine per 1 grain of titanium oxide is as follows. One gram of a titanium oxide sample dried at 130° C. for 2 hours is weighed in a 50-mL stoppered Erlenmeyer flask, and 30 mL of a n-butylamine solution diluted with methanol to have a normality of 0.003 N is added to the foregoing titanium oxide sample. Then, this is subjected to ultrasonic dispersion for 1 hour, and is left to stand for 10 hours. 10 mL of the supernatant fluid of the same is sampled. The sampled supernatant fluid is subjected to potentiometric titration using a perchloric acid solution diluted with methanol to have a normality of 0.003 N, and from the titrated amount of at the point of neutralization, the amount of adsorbed n-butylamine can be determined.

In the present method, the anatase-type titanium oxide having such a surface acidity that an amount of adsorbed n-butylamine per 1 gram of titanium oxide is 8 μmol or less preferably contains sodium as impurities in an amount of 1000 ppm by weight (wt ppm) or less. If the content of sodium as impurities is 1000 wt ppm or less, the deterioration of photocatalytic activity can be suppressed. The reason for this is uncertain, but it is assumed that, for example, sodium reacts with fluorine, whereby the inhibition of the reaction between fluorine and titanium oxide can be prevented.

Further, as an alkaline solution used at the stage of preparation of the starting material, and as additives to be added as required after the reaction with fluorine, those which substantially do not contain sodium are desirable. Examples of the alkaline solution include ammonia water, an aqueous ammonium carbonate solution, and an aqueous hydrazine solution.

In the present method, in the step of re-dispersing the filtration residue obtained by the filtration into water, the filtration residue preferably is in a state of not being dried when being re-dispersed into water. This is because the dispersibility of the filtration residue in the re-dispersion solution can be improved.

In the present invention, a specific method for obtaining the re-dispersion solution is not limited particularly. The re-dispersion solution may be prepared by, for example, any one of the methods shown below, or may be prepared by, for example, dispersing a powder-form titanium oxide available from the market (e.g., SSP-25 manufactured by SAKAI Chemical Industry Co., Ltd.) into pure water.

Method 1

An aqueous titanyl sulfate solution is heated to a temperature in a range of 80° C. to 100° C. so as to be hydrolyzed, and a slurry aqueous solution of white precipitate thus obtained is cooled. The pH of the obtained white precipitate slurry (aqueous dispersion solution of titanium oxide) is adjusted with ammonia water added to the slurry, until the pH becomes in a range of 7.5 to 9.5. Then, the slurry is filtered. The filtration residue thus obtained is washed with water thoroughly so that salts as impurities are removed. A cake made of this filtration residue thus obtained is re-dispersed in pure water, whereby a re-dispersion solution of an anatase-type titanium oxide can be obtained.

Method 2

After ammonia water is added to an aqueous titanyl sulfate solution, a pH of the obtained aqueous dispersion solution of titanium oxide is adjusted with ammonia water added to the dispersion solution until the pH becomes in a range of 7.5 to 9.5. Then, the slum is filtered. The filtration residue thus obtained is washed with water thoroughly so that salts as impurities are removed. A cake made of this filtration residue thus obtained is heated at 100° C., aged, and re-dispersed in pure water, whereby a re-dispersion solution of an anatase-type titanium oxide can be obtained.

Method 3

An aqueous titanium tetrachloride solution is heated so as to be hydrolyzed, and the pH of the obtained white precipitate slurry (aqueous dispersion solution of titanium oxide) is adjusted with ammonia water added to the slurry until the pH becomes in a range of 7.5 to 9.5. Then, the slurry is filtered The filtration residue thus obtained is washed with water thoroughly so that salts as impurities are removed. A cake made of this filtration residue thus obtained is heated to a temperature in a range of 80° C. to 100° C., aged, and re-dispersed in pure water, whereby a re-dispersion solution of an anatase-type titanium oxide can be obtained.

Method 4

Titanium tetraalkoxide is hydrolyzed in a solvent, and a pH of a suspension of the precipitate obtained (aqueous dispersion solution of titanium oxide) is adjusted by adding ammonia water to the suspension, until the pH becomes in a range of 7.5 to 93. Then, the suspension is filtered. The filtration residue thus obtained is washed with water thoroughly so that salts as impurities are removed. A cake made of this filtration residue thus obtained is heated to a temperature in a range of 80° C. to 100° C., aged, and re-dispersed in pure water whereby a re-dispersion solution of an anatase-type titanium oxide can be obtained.

The crystallinity of the anatase-type titanium oxide in the re-dispersion solution thus obtained preferably is such that a diffraction peak appears at a diffraction angle 2θ=25.5°, when it is measured by drying the re-dispersion solution at 50° C. under a reduced pressure so that dry powder is obtained, and measuring the crystallinity of the powder with a powder X-ray diffractometer using copper electrodes as working electrodes. This is because titanium oxide having such a characteristic is a crystallized anatase titanium oxide, and if this is used as a starting material, the photocatalytic activity can be improved.

In the present method, the fluorine compound to be added to the re-dispersion solution is not particularly limited, but examples of the same include ammonium fluoride, potassium fluoride, sodium fluoride, and hydrofluoric acid. Among these, ammonium fluoride, potassium fluoride, and hydrofluoric acid are preferred. When a fluorine compound is added to a re-dispersion solution, it is necessary to add a fluorine compound at least so that an amount of fluorine as an element becomes 2.5 wt % or more with respect to the titanium oxide photocatalyst obtained.

Examples of the method for adding the fluorine compound include a method of adding the above-described fluorine compound in a solid state to the re-dispersion solution, a method of adding an aqueous solution of the above-described fluorine compound to the re-dispersion solution, and a method of bubbling fluorine gas or hydrofluoric acid gas in the re-dispersion solution. Among these, from the viewpoint of cost efficiency and handleability, the method of adding the solid fluorine compound to the re-dispersion solution, and the method of adding an aqueous solution of the fluorine compound to the re-dispersion solution are preferable. Further, from the viewpoint of the efficiency of reaction between titanium oxide and fluorine, it is preferable that the re-dispersion solution obtained and the fluorine compound are mixed, without a hydrothermal treatment being carried out under such conditions that a specific surface area would not decrease. The time for the treatment for the fluorine compound is not limited particularly, but is preferably in a range of 5 minutes to 90 minutes. The time more preferably is in a range of 30 minutes to 60 minutes. In the case where the time is set at 5 minutes or more, the fluorine compound added is dispersed sufficiently. In the case where the time is set at 90 minutes or less, titanium oxide having high activity can be obtained. Further, the temperature for the treatment of the fluorine compound preferably is 40° C. or lower. In the case where the temperature is set at 40° C. or lower, a decrease in the specific surface area of titanium oxide can be prevented. The temperature for the treatment of a fluorine compound normally is 10° C. or higher.

In the present invention, examples of acid used for the adjustment of a pH include hydrochloric acid, nitric acid, sulfuric acid, and hydrofluoric acid. An upper limit of the pH of a suspension obtained by adding a fluorine compound to a re-dispersion solution of titanium oxide and a mixed solution containing the anatase-type titanium oxide and a fluorine compound is 3 or less. A lower limit of the pH of the suspension and the mixed solution is not limited particularly, but from the viewpoint of cost efficiency and handleability, the pH preferably is 1 or more.

In the present invention, a reaction product obtained through the reaction step is washed with, for example, water. This makes it possible to remove fluorine that has not reacted with titanium oxide in the reaction step, unnecessary salts, dissolved impurities, and the like. Therefore, the photocatalytic activity can be improved.

In the case where the washing is carried out with water (water washing), the washing preferably is carried out until an electric conductivity of water used in the washing becomes 1 mS/cm or less, as an index for washing. In the case where the washing is carried out until an electric conductivity of water used in the washing becomes 1 mS/cm or less, unnecessary salts, dissolved impurities, etc. can be removed adequately. Here, immediately after the treatment with a fluorine compound, the washing preferably is carried out with the treatment liquid with the same liquid composition, without the pH thereof being adjusted. This is because the washing with the treatment liquid with the same liquid composition makes it possible to remove impurities dissolved in the liquid easily, and hence, improves the photocatalytic activity. It should be noted that as the washing method, a method using a centrifuge, filtration equipment of any one of various types, a rotary washing machine or the like can be used, for example.

In the present method, the titanium oxide photocatalyst obtained as described above may be subjected to a finishing treatment as required, depending on the use of the photocatalyst. For example, in the case where the photocatalyst is finished into a powder form through a drying step, it may be subjected to any conventionally known treatment for avoiding the aggregation caused by the drying, and any means for loosening aggregated powder may be used. In order to loosen powder aggregated due to the drying, any common grinder may be used, but the grinding has to be carried out under such conditions that the photocatalytic activity would not deteriorate. For example, in order to prevent titanium oxide crystals from being destroyed, the grinding power has to be decreased.

Further, the titanium oxide photocatalyst having been washed through the above-described washing step may be dispersed in a solvent again so as to be used as an aqueous, oily, or emulsified dispersion solution. Here, a wet-type grinder may be used in order to loosen caking, but a type of equipment and conditions that would not deteriorate the photocatalytic activity have to be chosen, as described above. For example, in the case of a dispersing device using a grinding medium, the concentration of titanium oxide preferably is increased in order to prevent the mixing of impurities caused by the abrasion of the medium. A diameter of the medium preferably is decreased in order to avoid the destruction of crystals of titanium oxide caused by the impact of the medium.

Additionally, a surface treatment may be performed as required, depending on the use of the photocatalyst. In this case, examples of a commonly known method for this include a method of causing titanium oxide to support, on its surfaces, an adsorption component or an adsorbent such as silica, apatite, or zeolite, or contrarily, a method of causing titanium oxide to be supported by an adsorbent. In the case where a surface treatment is applied in this manner, materials used in the treatment have to be selected so that no deterioration of the photocatalytic activity should be caused or the deterioration ratio should fall in a tolerable range.

Zeolite used in the present invention is, for example, a zeolite in which silica and alumina are bonded with each other via oxygen, and typical crystalline forms thereof are the A form, the X form, the beta form, the ferrite form, the mordenite form, the L form, and the Y form. Various types of zeolite having different pore diameters and different shapes can be synthesized by varying the molar component ratio between silica and alumina (hereinafter this ratio also is referred to as "silica/alumina ratio") and the calcining temperature. It should be noted that a normal zeolite has a particle diameter of 1 to 20 μm and a pore diameter of 0.1 nm to 1 nm.

In view of the photocatalytic activity and the filter recycling to be described later, the mordenite-form zeolite or the ZSM-5-form zeolite is used preferably as the zeolite. The mordenite-form zeolite (structure code: MOR) generally refers to an orthorhombic-system zeolite that has a unit cell composition of $Na_8[Al_8Si_{40}O_{96}]\cdot 24H_2O$ and 12-membered-ring two-dimensional pores (effective diameter: 0.6 nm). The ZSM-5-form zeolite (structure code: MFI) generally refers to an orthorhombic-system zeolite that has a unit cell composition of $Na_n[Al_nSi_{96-n}O_{191}]\cdot xH_2O$ (n<27) and 10-membered-ring two-dimensional pores (effective diameter: 0.6 nm).

In the present invention, the function of zeolite is to cause odorous components to get closer to titanium oxide having photocatalytic activity so as to concentrate the odorous components. Therefore, zeolite that exhibits higher performance of adsorbing odorous components is used preferably. Particularly, zeolite capable of adsorbing acetaldehyde is desirable. This is because, among odorous components, acetaldehyde is a component that cannot be adsorbed fully by conventional active carbon and is contained in various types of offensively odorous components. For example, a high-silica/alumina-ratio zeolite is preferable, which exhibits high ability of adsorbing acetaldehyde, and the mordenite-form zeolite having a crystal structure with a pore diameter of about 0.5 nm is more preferable. Further, in order to enhance the odorous component adsorbing property, the silica/alumina ratio of zeolite is, for example, 150 or more, and from the viewpoint of further enhancing the photocatalytic activity, it preferably is 200 or more, more preferably 240 or more, further preferably 1500 or more, and still further preferably 1890 or more. The upper limit of the silica/alumina ratio is, for example, 10000 or less. The pore diameter of zeolite is, for example, 7 Å or less, and from the viewpoint of enhancing the performance of adsorbing organic molecules, it preferably is 4 to 6 Å. The pore diameter of zeolite can be measured by, for example, image observation with a transmission electron microscope (TEM).

As zeolite, commercially available zeolite may be used Examples of the commercially available zeolite include HSZ-690HOA (manufactured by Tosoh Corporation, mordenite form, silica/alumina ratio: 240, average particle diameter: 13 μm, cation type: H, specific surface area (BET); 450 m$^2$/g); HSZ-890HOA (manufactured by Tosoh Corporation, ZSM-5 form, silica/alumina ratio: 1500 to 2000 (average: 1890), average particle diameter: 8 to 14 pun, cation type: H, specific surface area (BET): 280 to 330 m$^2$/g); ABSCENTS™-1000 (manufactured by Union Showa K.K., average particle diameter: 3 to 5 μm, cation type: Na); ABSCENTS™-2000 (manufactured by Union Showa K.K., average particle diameter; 3 to 5 am, cation type: Na); Smellrite™ (manufactured by Union Showa K.K., average particle diameter: 3 to 5 μm, cation type; Na); and HiSiv™-3000 (manufactured by Union Showa K.K., average particle diameter: 12.7 μm, cation type: Na, pore diameter: 6 Å or less, specific surface area (BET): 400 m$^2$/g or more). Each of ABSCENTS™-1000, ABSCENTS™-2000, and Smellrite™ contains a plurality of zeolites including a mordenite-form zeolite, and the ratio of the mordenite-form zeolite therein is 90% or more. It should be noted that the average particle diameter of zeolite in the present invention refers to a particle diameter at a cumulative volume percentage of 50%, which can be determined by, for example, a laser diffraction/diffusion method.

With the photocatalytic material of the present invention, it is possible to decompose odorous components to a concentration lower than that achieved by a conventional composite photocatalyst containing an adsorbent and a photocatalyst (e.g. JP 1(1989)-118635 A, JP 2002-136811 A, and JP 11(1999)-319570 A), so as to achieve deodorization, and preferably, it is possible to decompose acetaldehyde, which is contained much in smoke of tobacco products. Further, the photocatalytic material of the present invention is capable of recovering its ability of adsorbing and/or decomposing odorous components when irradiated with light. Therefore, with the photocatalytic material of the present invention, for example, a filter can be realized whose ability of adsorbing and/or decomposing odorous components can be recovered by irradiation of light for about 2 hours per one day, and preferably, a maintenance-free air purification device can be realized that does not need maintenance of a filter. Light to be irradiated may be any light as long as it contains light having an energy higher than the band gap of the titanium oxide photocatalyst, and it may be ultraviolet rays, preferably light having a wavelength of 380 nm or less, and more preferably black light having a center wavelength in the vicinity of 352 nm.

The content of zeolite in the photocatalytic material of the present invention (zeolite/(zeolite+titanium oxide photocatalyst)) is, for example, 10 wt % or more; preferably 10 to 90 wt %; more preferably 20 to 80 wt % from the viewpoint of enhancing the photocatalytic activity; and further preferably 20 to 50 wt %.

The photocatalytic material of the present invention is obtained by mixing the above-described titanium oxide photocatalyst and zeolite by, for example, dry mixing, ball-mill mixing, or wet mixing. Here, in order to enhance the ability of adsorbing odorous components, the mixing is carried out preferably so that the content of zeolite in the photocatalytic material is 10 wt % or more, and more preferably 30 wt % or more. Besides, in order to enhance the photocatalytic activity, the mixing is carried out preferably so that the content of zeolite in the photocatalytic material is 90 wt % or less, and more preferably 40 wt % or less.

The average particle diameter of the photocatalytic material of the present invention is, for example, 5 μm or less, and from the viewpoint of enhancing the deodorization rate, preferably 1.8 μm or less, more preferably 1.5 μm or less, and further preferably 1 μm or less. In the present invention, the average particle diameter of the photocatalytic material refers to a particle diameter at a cumulative volume percentage of 50%, which can be determined by, for example, a laser diffraction/diffusion method.

Next, a photocatalytic member of the present invention is described below. The photocatalytic member of the present invention includes a substrate and a photocatalyst layer formed on a surface of the substrate, wherein the photocatalyst layer contains the above-described photocatalytic material of the present invention. With this, for example, the performance of decomposing odorous components and the rate of decomposing the same can be enhanced, for the same reason as described above.

The photocatalytic member of the present invention is obtained by applying a photocatalytic material over a substrate made of glass or ceramics, the photocatalytic material being obtained by mixing the above-described titanium oxide photocatalyst and zeolite. The application may be carried out in the following manner: a photocatalytic material is dispersed in a solvent such as water or ethyl alcohol, and is applied over a substrate; or a mixture of a photocatalytic material and an inorganic hinder is applied over a substrate. The use of an inorganic binder is preferable since it enhances adhesion of a photocatalytic material to a substrate. It should be noted that examples of the inorganic hinder include tetraethoxysilane (TEOS) and colloidal silica. Examples of the application method include slurry application, spin coating, spraying, and casting coating.

In the photocatalytic member of the present invention, the content of the photocatalytic material in the photocatalyst layer preferably is in a range of 50 to 100 wt % in order to enhance the photocatalytic activity. The photocatalyst layer may contain other components than the above-described photocatalytic material, such as an inorganic binder, $WO_3$, $H_2Ti_4O_2$, TiOS, TiON, and $SiO_2$. The content of these other components in the photocatalyst layer is in a range of, for example, 0 to 50 wt %. It should be noted that the thickness of the photocatalyst layer is not limited particularly, but it desirably is about 100 to 500 μm, through which light can penetrate. Further, the thickness of the substrate is not limited particularly, but is about 0.1 to 2 mm, for example.

If an air permeable substrate is used as the substrate in the photocatalytic member of the present invention, the photocatalytic member of the present invention can be used as a gas permeable filter for the purpose of deodorization. Examples of the substrate having air permeability include nonwoven fabrics, glass fibers, foamed metals, porous ceramics, and foamed resins.

Next, a purification device of the present invention is described below. The purification device of the present invention is a purification device that includes the above-described photocatalytic member of the present invention, and a light source that irradiates the photocatalytic member with light having a wavelength of 400 nm or less. With this, for example, the performance of decomposing odorous components and the rate of decomposing the same can be enhanced, for the same reason as described above. Preferable examples of the foregoing light source will be described later.

The purification device of the present invention may be provided further with blowing means that introduces a gas containing organic substances into the photocatalytic member. This is because this configuration makes it possible to use the purification device of the present invention as an air purification device capable of decomposing organic substances in air at a high rate. It should be noted that the blowing means is not limited particularly, and a blower such as a sirocco fan may be used, for example.

The purification device of the present invention further may include liquid feeding means that introduces a liquid containing organic substances into the photocatalytic member. This is because this configuration makes it possible to use the purification device of the present invention as a liquid purification device capable of decomposing organic substances in the liquid at a high rate. Preferable examples of the foregoing liquid feeding means will be described later.

Hereinafter, embodiments of the present invention will be described below, with reference to the drawings. It should be noted that the same constituent elements are designated with the same reference numerals, and descriptions of the same are omitted in some cases.

Embodiment 1

FIG. 1 is a cross-sectional view of a photocatalytic member according to Embodiment 1 of the present invention. As shown in FIG. 1, the photocatalytic member 1 includes a substrate 10, and a photocatalyst layer 11 formed on one of principal faces of the substrate 10. The photocatalyst layer 11 contains the above-described photocatalytic material of the present invention. If the substrate 10 is made of a material that transmits ultraviolet rays, such as glass, quartz, or a fluorocarbon resin, a light source (not shown) can be disposed on a side of the other principal face so as to be isolated from a substance to be treated, whereby the light source can be prevented from being contaminated. It should be noted that the substrate 10 used in the present embodiment might be any material other than a material that transmits ultraviolet rays, as long as it is not degraded by ultraviolet rays. Examples of the material that is not degraded by ultraviolet rays include ceramics such as silica, inorganic materials such as metals, and organic materials such as acrylic resins and urethane resins. The shape of the photocatalytic member 1 also is not limited, and the photocatalytic member 1 may be in a particulate form in which particles have a spherical shape, a polygonal shape, or different shapes in combination; in a sheet form of nonwoven or woven fabric; or in a porous form, a three-dimensional foamed form, a honeycomb form, or a pleated form. Further, as in Embodiment 2 described later, the photocatalyst layers 11 may be provided on both of the principal faces of the substrate 10. The photocatalytic member 1 shown in FIG. 1 may be used in, for example, a co-flow air purification device.

Figure 2A:
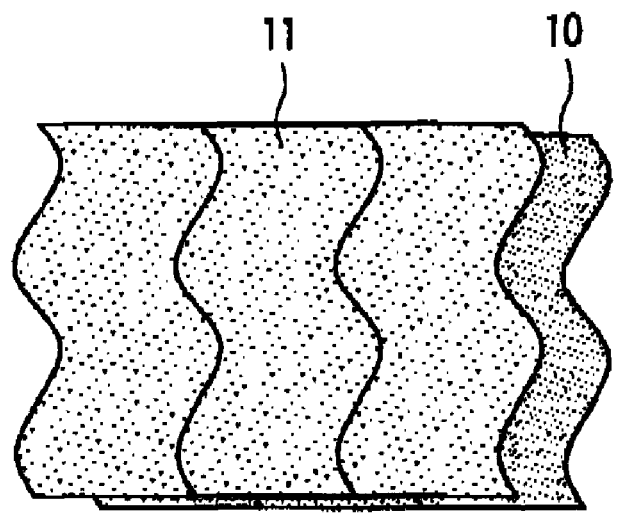
FIGS. 2A and 2B are perspective views of typical gas-permeation filters of the present invention.
Figure 2B:
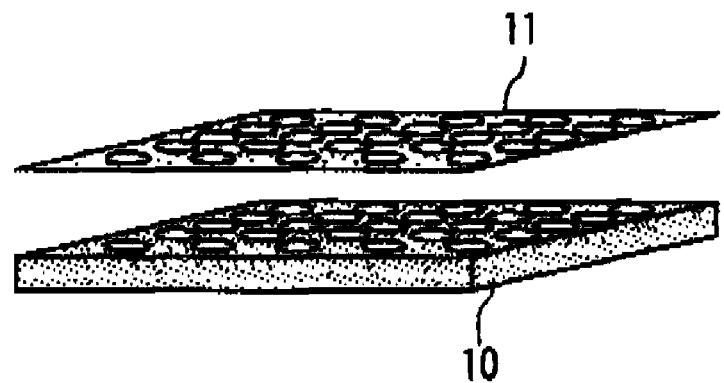

Further, if the substrate having air permeability is used as the substrate 10 in the photocatalytic member 1, the photocatalytic member 1 can be used as a gas-permeable filter for the purpose of deodorization. Examples of the substrate having air permeability include nonwoven fabrics, glass fibers, foamed metals, porous ceramics, and foamed resins. FIGS. 2A and 2B show perspective views of typical gas-permeable filters of the present invention.

Embodiment 2

Figure 3:
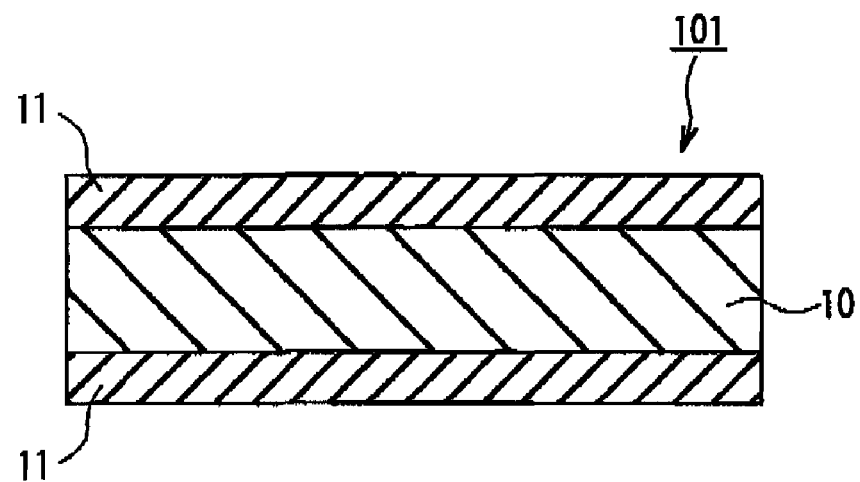
FIG. 3 is a perspective view of a photocatalytic member according to Embodiment 2 of the present invention.

FIG. 3 is a cross-sectional view of a photocatalytic member according to Embodiment 2 of the present invention. As shown in FIG. 3, the photocatalytic member 101 includes a substrate 10, and photocatalyst layers 11, 11 formed on both of principal faces of the substrate 10. The photocatalyst layers 11 has a titanium oxide photocatalyst and zeolite, the titanium oxide photocatalyst containing at least an anatase-type titanium oxide and fluorine, wherein the content of the fluorine in the titanium oxide photocatalyst is 2.5 wt % to 3.5 wt %, and 90 wt % or more of the fluorine is bonded chemically with the anatase-type titanium oxide. With this, the photocatalytic activity is enhanced, and the rate of decomposition of odorous components, for example, can be enhanced. It should be noted that the photocatalyst layer in every embodiment described hereinafter has the same constitutional elements as those of the above-described photocatalyst layer 11.

The substrate 10 may be made of, for example, a mesh filter sheet composed of warp and weft made of twisted strings of glass fibers. The photocatalyst layer 11 contains, for example, an inorganic binding agent such as silica sol, and the like, other than the above-described titanium oxide photocatalyst.

Embodiment 3

Figure 4:
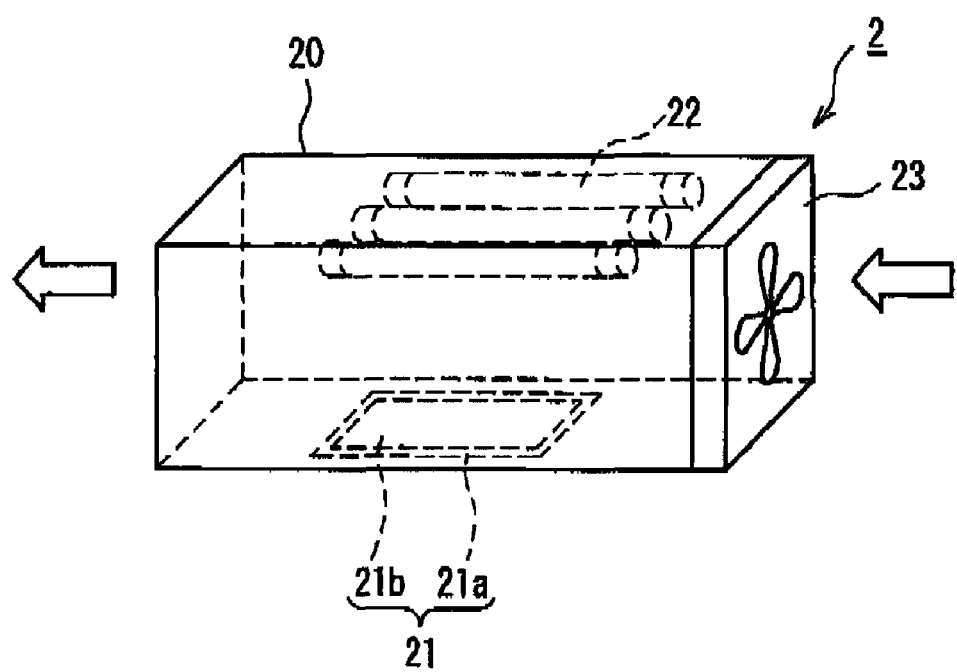
FIG. 4 is a perspective view of a purification device according to Embodiment 3 of the present invention.

FIG. 4 is a perspective view of a purification device according to Embodiment 3 of the present invention. As shown in FIG. 4, a co-flow air purification device 2 includes a container 20, a photocatalytic member 21 provided on a bottom face of the container 20, light sources 22 that are disposed in the container 20 so as to face the photocatalytic member 21, and blowing means 23 that blows odorous components in the container 20 toward the photocatalytic member 21. The photocatalytic member 21 includes a substrate 21a, and a photocatalyst layer 21b formed on the substrate 21a. The photocatalyst layer 21b contains the above-described photocatalytic material of the present invention. The container 20 is made of for example, a metal, a resin, or the like. As the light sources 22, black lights having a wavelength of 352 nm at the maximum irradiation intensity, or cold-cathode tubes, can be used. The light intensity of the light sources 22 is, for example, 1 mW/cm$^2$ or more, and it is possible to increase the activity degree of the photocatalyst by increasing the light intensity. On the other hand, from the viewpoints of the uniformity of light, the power consumption, and the lifetime, the light intensity preferably is about 0.5 mW/cm$^2$ to 5 mW/cm$^2$. It should be noted that the distance between the light sources 22 and the photocatalyst layer 21b may be about 1 to 20 cm.

The co-flow air purification device 2 may be used in the following manner. First, a gaseous substance is introduced toward the photocatalytic member 21 with the blowing means 23, so that the photocatalyst layer 21b adsorbs the gaseous substance. The light sources 22 irradiate the photocatalyst layer 21b with ultraviolet rays, so that the gaseous substance is decomposed oxidatively. Here, the irradiation of the photocatalyst layer 21b with ultraviolet rays may be carried out after the gaseous substance is adsorbed by the photocatalyst layer 21b, or the adsorption of the gaseous substance and the irradiation of ultraviolet rays may be carried out concurrently. It should be noted that an amount of air blown by the blowing means 23 may be set in a range of, for example, 0.5 to 2 m/s.

Embodiment 4

Figure 5:
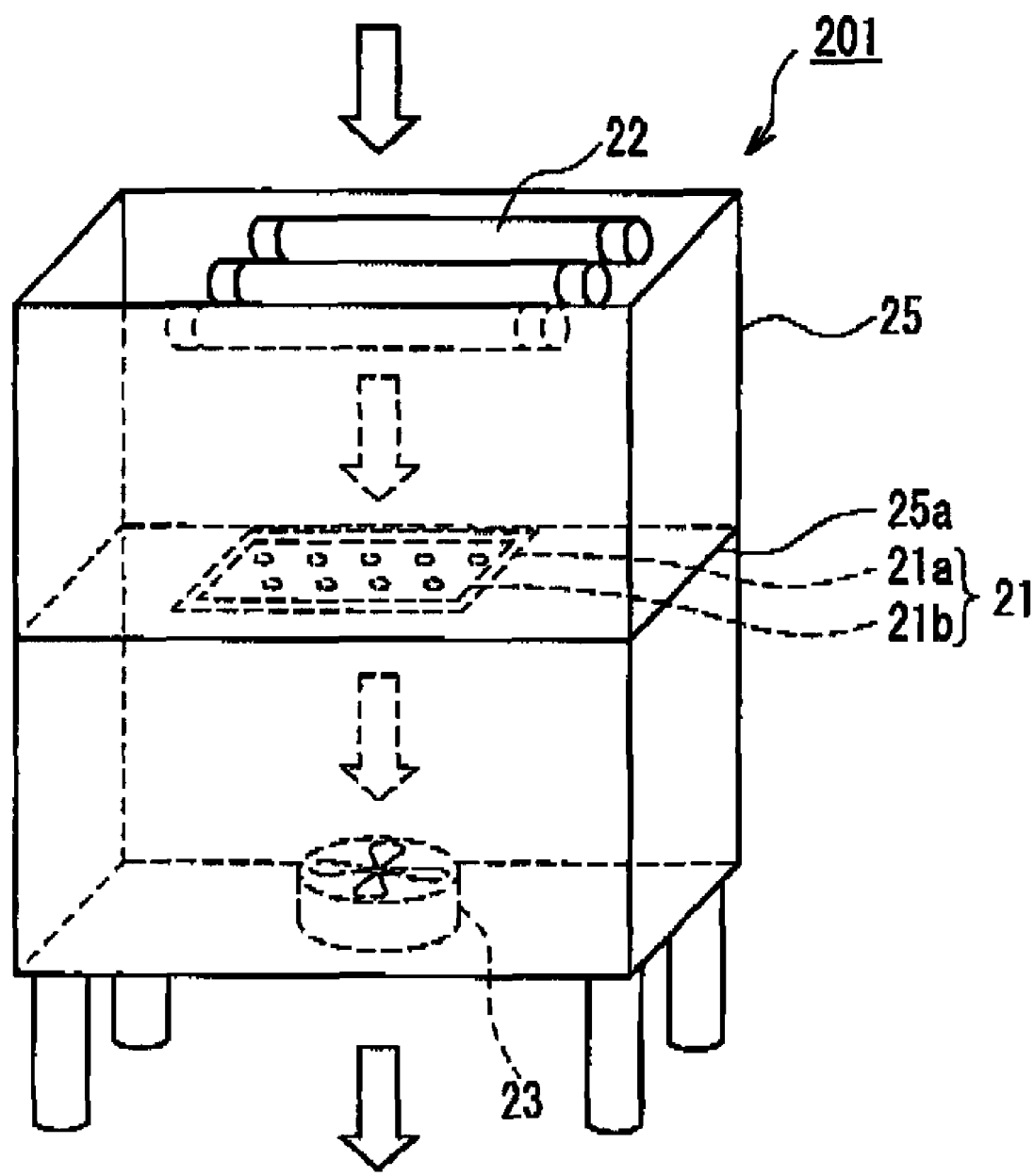
FIG. 5 is a perspective view of a purification device according to Embodiment 4 of the present invention.

FIG. 5 is a perspective view of a purification device according to Embodiment 4 of the present invention. As shown in FIG. 5, a cross-flow air purification device 201 includes a container 25, a photocatalytic member 21 disposed on a parting plate 25a provided in the container 25, light sources 22 that are disposed in the container 25 so as to face the photocatalytic member 21, and blowing means 23 that is provided at a lowermost part of the container 25 and introduces odorous components toward the photocatalytic member 21. Outer walls of the container 25 are formed with, for example, a metal or a resin. The parting plate 25a is formed with a substrate having air permeability, such as a punched metal plate. As a substrate 21a of the photocatalytic member 21, a substrate having air permeability can be used, such as a substrate made of a nonwoven fabric, a glass fiber, a foamed metal, a porous ceramics, a foamed resin, or the like. It should be noted that the method of using the cross-flow air purification device 201 is the same as that of the co-flow air purification device 2 described above.

Embodiment 5

Figure 6A:
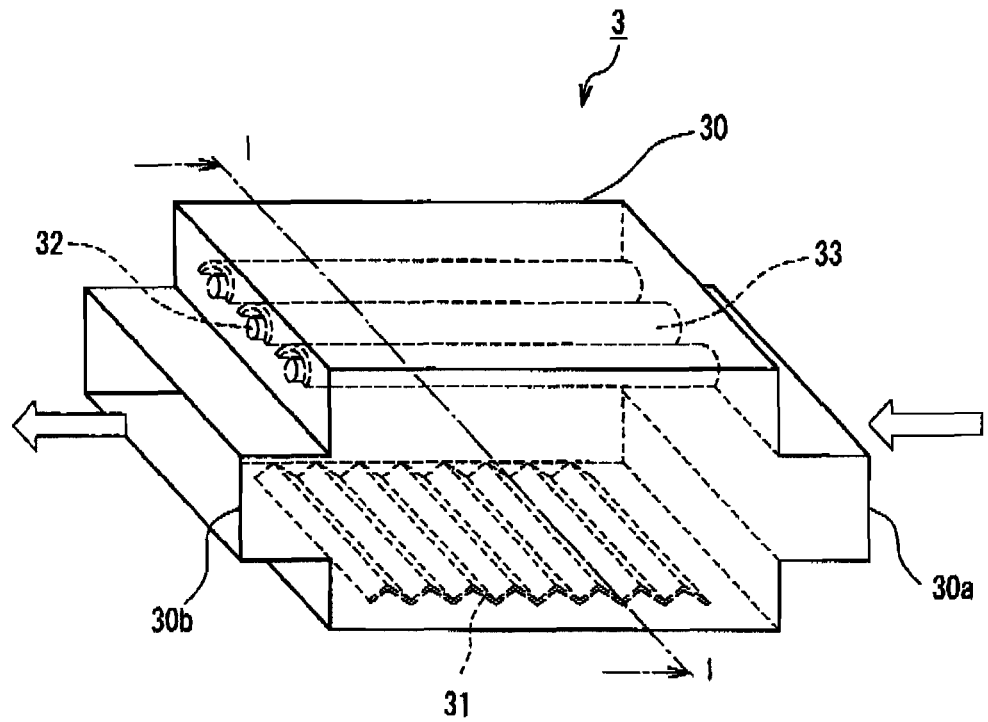
FIG. 6A is a perspective view of an air purification device according to Embodiment 5 of the present invention.
Figure 6B:
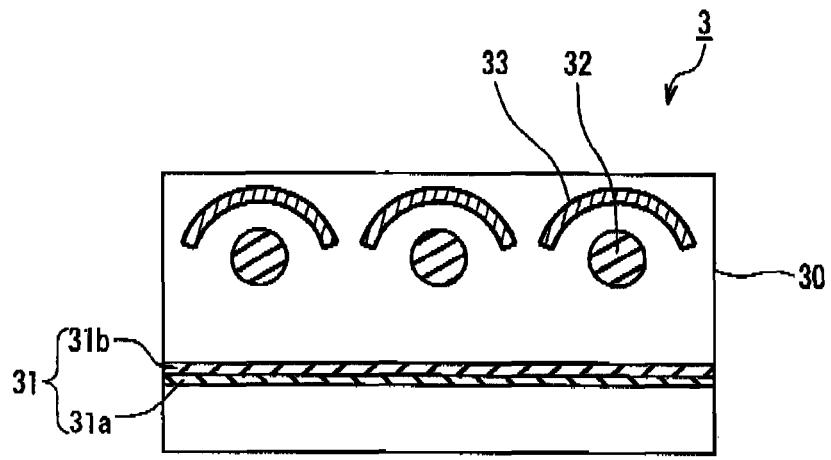
FIG. 6B is a cross-sectional view of the device shown in FIG. 6A, taken along a line I-I.

FIG. 6A is a perspective view of an air purification device according to Embodiment 5 of the present invention, and FIG. 6B is a cross-sectional view of the same taken along a line I-I shown in FIG. 6A. As shown in FIGS. 6A and 6B, the air purification device 3 includes a container 30, a photocatalytic member 31 provided at a bottom of the container 30, and light sources 32 that irradiate the photocatalytic member 31 with light having a wavelength of 400 nm or less. Between a ceiling face of the container 30 and the light sources 32, semi-cylindrical reflection plates 33 are provided so that light from the light sources 32 is projected uniformly over the photocatalytic member 31. It should be noted that the reflection plates 33 are made of, for example, stainless steel, aluminum, or the like. Further, the container 30 is made of, for example, a metal, a resin, or the like.

As shown in FIG. 6B, the photocatalytic member 31 includes a substrate 31a made of ceramics or the like, and a photocatalyst layer 31b formed on a light-source-32-side principal face of the substrate 31a. Further, as shown in FIG. 6A, the photocatalytic member 31 is in a pleated form so that an area where the photocatalytic reaction occurs is expanded. It should be noted that the photocatalyst layer 31b is formed on the substrate 31a by spreading, slurry coating, or another means. Further, the photocatalyst layer 31b may contain, for example, several percents by weight of an inorganic binder or the like so that the adhesion thereof to the substrate 31a is enhanced.

As the light sources 32, black lights having a wavelength of 352 nm at the maximum irradiation intensity or cold cathode tubes, for example, may be used. The light intensity is, for example, 1 mW/cm$^2$ or more, and the activity of the photocatalyst can be increased by increasing the light intensity. However, from the viewpoints of the uniformity of light, the power consumption, and the lifetime, the light intensity preferably is about 0.5 mW/cm$^2$ to 5 mW/cm$^2$. It should be noted that the distance between the light sources 32 and the photocatalyst layer 31b may be about 1 to 20 cm.

The air purification device 3 can be used in a relative narrow space or in an air circulation path. For example, the device can be used suitably in a cold air circulation path of a refrigerator, a dust box of a vacuum cleaner, etc. In this case, when the photocatalyst layer 31b of the photocatalytic member 31 is irradiated with ultraviolet rays from the light sources 32, the photocatalyst layer 31b is activated. In this state, when a gas containing organic substances such as odors of the inside of the refrigerator or the vacuum cleaner, for example, is fed via an inlet 30a of the container 30 and comes into contact with the photocatalyst layer 31b, the organic substances are decomposed oxidatively, whereby the gas becomes a less odorous gas and goes out via an outlet 30b of the container 30. This is carried out repetitively, whereby air around the air purification device 3 is purified.

Embodiment 6

Figure 7:
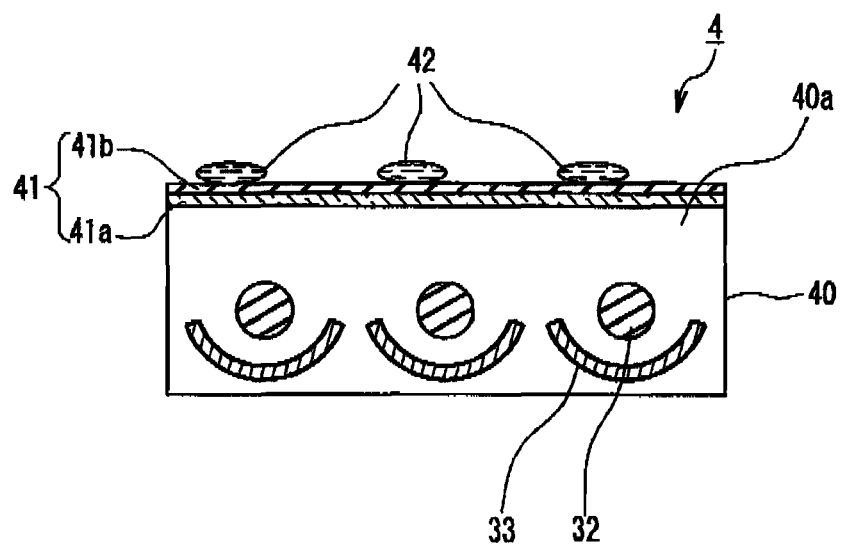
FIG. 7 is a cross-sectional view of an air purification device according to Embodiment 6 of the present invention.

FIG. 7 is a cross-sectional view of an air purification device according to Embodiment 6 of the present invention. As shown in FIG. 7, the air purification device 4 includes a container 40 having an opening 40a, a photocatalytic member 41 disposed so as to cover the opening 40a, and light sources 32 that are disposed at a bottom of the container 40 and irradiate the photocatalytic member 41 with light having a wavelength of 400 nm or less. Further, between the bottom face of the container 40 and the light sources 32, semi-cylindrical reflection plates 33 are provided so that light from the light sources 32 is projected uniformly over the photocatalytic member 41.

The photocatalytic member 41 includes a substrate 41a made of a material that permeates ultraviolet rays (e.g. glass), and a photocatalyst layer 41b provided on a principal face of the substrate 41a on a side opposite to the light sources 32. Thus, the air purification device 4 of the above-described embodiment is configured so that the light sources 32 are surrounded by the container 40 and the photocatalytic member 41, whereby the light sources 32 are prevented from being contaminated. For example, a maintenance-free cooker hood can be provided if the air purification device 4 is disposed in an airflow path of the cooker hood, in which oil mist flows. In this case, the photocatalyst layer 41b of the photocatalytic member 41 is activated when irradiated with ultraviolet rays from the light sources 32. In this state, when oil mist 42, for example, comes into contact with the photocatalyst layer 41b, the oil mist 42 is decomposed oxidatively, whereby the surface of the photocatalytic member 41 is returned into an original clean state.

Embodiment 7

Figure 8:
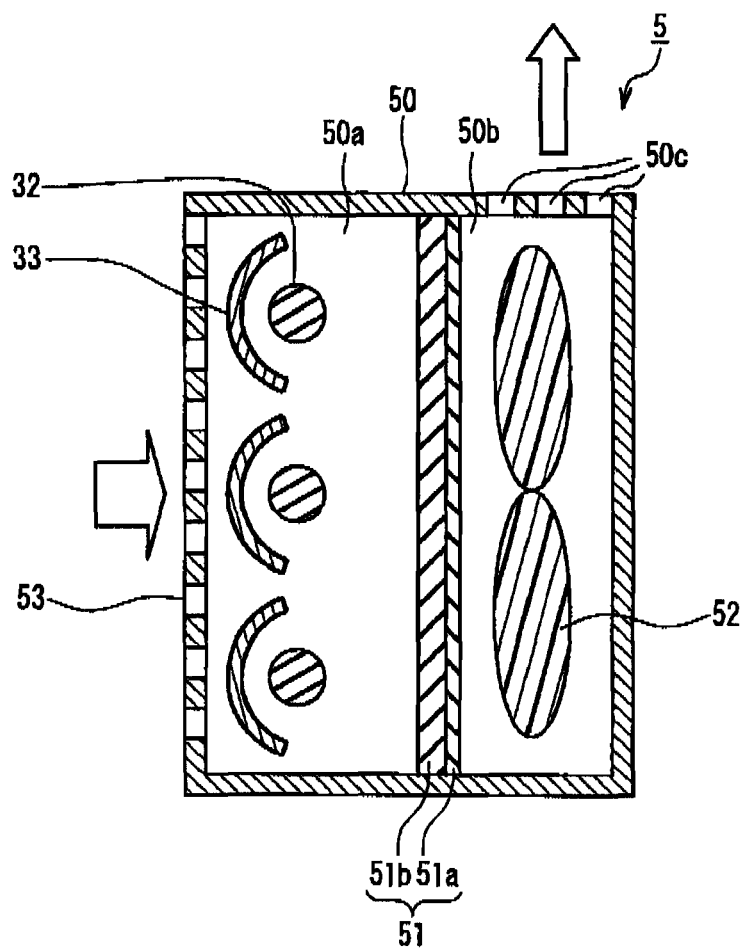
FIG. 8 is a cross-sectional view of an air purification device according to Embodiment 7 of the present invention.

FIG. 8 is a cross-sectional view of an air purification device according to Embodiment 7 of the present invention. As shown in FIG. 8, the air purification device 5 includes a container 50, a photocatalytic member 51 that divides the inside of the container 50 into a compartment 50a and a compartment 50b, light sources 32 that are disposed in the compartment 50a and irradiate the photocatalytic member 51 with light having a wavelength of 400 nm or less, and blowing means 52 that is disposed in the compartment 50b and introduces a gas containing organic substances toward the photocatalytic member 51. A wall part of the compartment 50a on a side opposite to the photocatalytic member 51 is made of a prefilter 53, and semi-cylindrical reflect on plates 33 are disposed between the prefilter 53 and the light sources 32 so that the light from the light sources 32 is projected uniformly over the photocatalytic member 51.

The photocatalytic member 51 includes an air-permeable substrate 51a, and a photocatalyst layer 51b provided on a principal surface of the substrate 51a on the light-source-32 side. As the blowing means 52, a sirocco fan or the like can be used.

The air purification device 5 of Embodiment 7 can be used as an air vivification device, a deodorizing machine, a purification device for a semiconductor clean room, or an industrial VOC (volatile organic compound) purification device for use in a printing plant or a paint plant. In this case, when the photocatalyst layer 51b of the photocatalytic member 51 is irradiated with ultraviolet rays from the light sources 32, the photocatalyst layer 51b is activated. In this state, the blowing means 52 is driven, and a gas containing organic substances such as odors in the room, VOC, fungus, etc. comes in through the prefilter 53. When the gas comes into contact with the photocatalyst layer 51b, the organic substances in the gas are decomposed oxidatively, and the gas becomes purified, then going out via an outlet 50c provided in a wall of the compartment 50b. This is carried out repetitively, whereby air around the air purification device 5 is purified.

Embodiment 8

Figure 9:
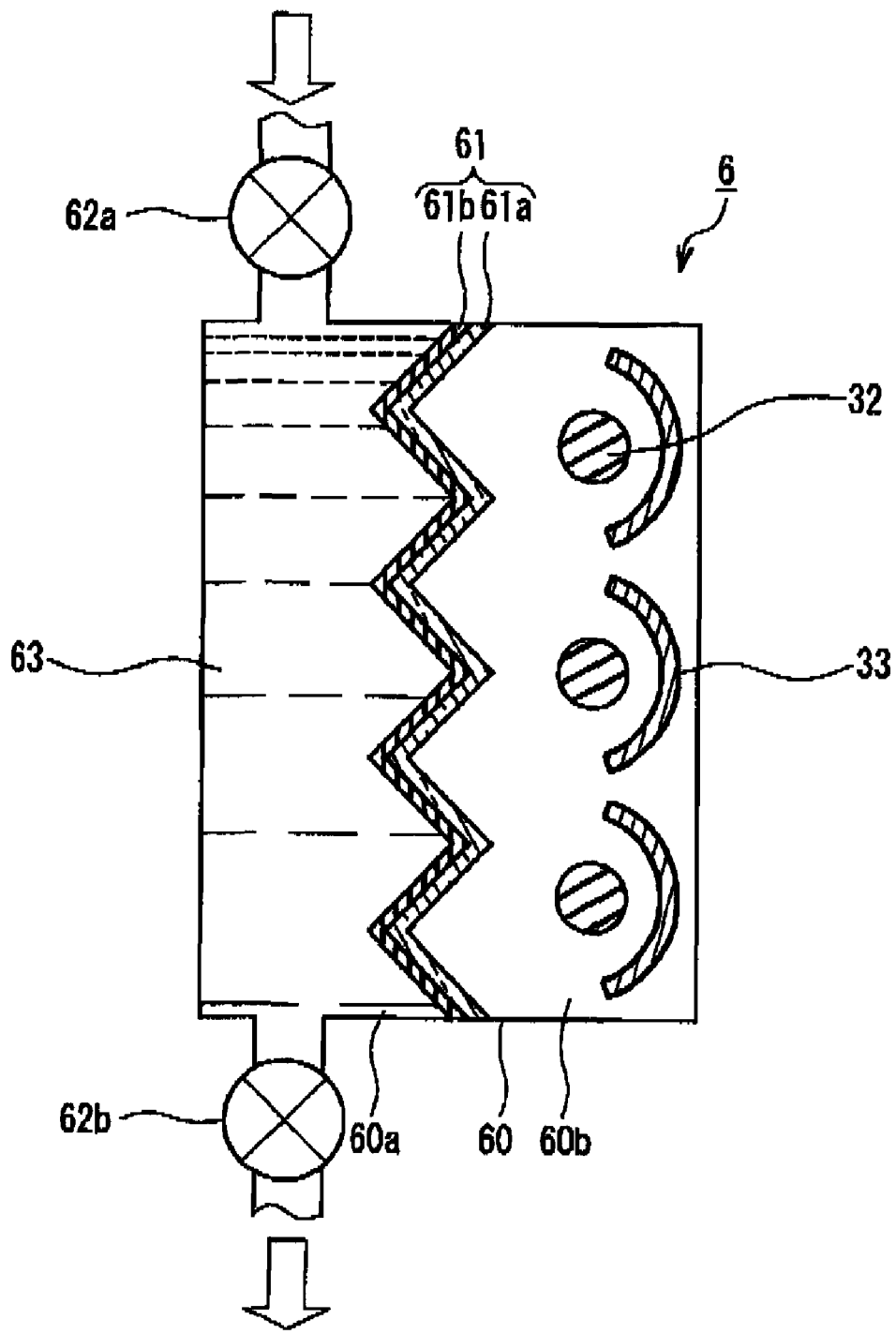
FIG. 9 is a cross-sectional view of a liquid purification device according to Embodiment 8 of the present invention.

FIG. 9 is a cross-sectional view of a liquid purification device according to Embodiment 8 of the present invention. As shown in FIG. 9, the liquid purification device 6 includes a container 60, a photocatalytic member 61 that divides the inside of the container 60 into a compartment 60a and a compartment 60b, a liquid-feeding valve 62a and a liquid-discharging valve 62b provided in walls of the compartment 60a, and light sources 32 that are disposed in the compartment 60b and irradiate the photocatalytic member 61 with light having a wavelength of 400 nm or less. Further, between the light sources 32 and a wall face of the compartment 60b on a side opposite to the photocatalytic member 61, semi-cylindrical reflection plates 33 are provided so that light from the light sources 32 is projected uniformly over the photocatalytic member 61.

The photocatalytic member 61 includes a substrate 61a made of a material that transmits ultraviolet rays (e.g. glass), and a photocatalyst layer 61b provided on a principal face of the substrate 61a on a side thereof opposite to the light-source-32 side. The photocatalytic member 61 is in a pleated form so that an area where the photocatalytic reaction occurs is expanded.

The liquid purification device 6 according to Embodiment 8 is a batch-type purification device that purifies, by natural retention, contaminated water 63 introduced in the compartment 60a. For example, this is suitable for, for example, a domestic purification pot, and is effective for decomposing and removing frowzy odor, trihalomethane, etc. In this case, when water is fed into the compartment 60a and the photocatalyst layer 61b of the photocatalytic member 61 is irradiated with ultraviolet rays from the light source 32, the photocatalyst layer 61b is activated. In this state, when organic substances such as the frowzy odor, trihalomethane, etc. in, water that is being purified come into contact with the photocatalyst layer 61b, the organic substances are decomposed oxidatively, whereby the water is cleaned. It should be noted that if liquid-feeding means (not shown) such as a pump for feeding contaminated water from the liquid-feeding valve 62a to the compartment 60a is disposed, for example, outside the container 60, organic substances in the contaminated water can be decomposed at a high rate.

EXAMPLES

Hereinafter, Examples of the present invention will be described together with Reference Examples and Comparative Examples. It should be noted that the present invention is not limited to the following Examples.

Reference Example 1

A solution of titanyl sulfate (manufactured by SAKAI Chemical Industry Co., Ltd.) in which the concentration as to titanium oxide was 100 g/L and the concentration as to sulfuric acid was 250 g/L was kept at 100° C. for 3 hours to be hydrolyzed thermally. The pH of the obtained slurry aqueous solution was adjusted with ammonia water until the pH became 8.0, and was filtered. Then, the substance obtained by filtration was washed thoroughly with water to remove salts as impurities. Here, the water washing was performed until the electric conductivity of the washing liquid became 200 µS/cm. Pure water was added to the cake thus obtained so that the concentration of the titanium oxide therein would become 150 g/L, and was stirred, whereby a re-dispersion solution of the titanium oxide was prepared. After that, hydrofluoric acid (manufactured by Wako Pure Chemical Industries, Ltd., guaranteed reagent) equivalent to 5.0 wt % in terms of fluorine (element) with respect to titanium oxide was added to this re-dispersion solution so as to cause a reaction at 25° C. for 60 minutes while the pH thereof was kept at 3. The obtained reaction product was washed thoroughly with water to remove salts as impurities. Here, the water washing was performed until the electric conductivity of the washing liquid became 1 mS/cm or less. Then, this was dried in air at 130° C. for 5 hours so as to be powdered, whereby a titanium oxide photocatalyst of Reference Example 1 was obtained. The titanium oxide photocatalyst of Reference Example 1 had a specific surface area of 259 $m^2/g$ (determined by the BET method). Further, regarding the obtained titanium oxide photocatalyst, the amount of eluted fluorine was measured by a measuring method to be described later, and was found to be 5 wt %. That is, 95 wt % of fluorine in the titanium oxide photocatalyst was bonded chemically to the anatase-type titanium oxide. It should be noted that a part of the above re-dispersion solution was dried at 50° C. under a reduced pressure so as to be powdered, and the amount of n-butylamine adsorbed by the obtained powder was measured by the aforementioned measuring method. The amount was found to be 2 µmol/g.

Reference Example 2

A titanium oxide photocatalyst of Reference Example 2 was obtained in the same manner as in Reference Example 1 described above, except that a hydrofluoric acid (manufactured by Wako Pure Chemical Industries, Ltd., guaranteed reagent) equivalent to 7.5 wt % in terms of fluorine (element) was used as a hydrofluoric acid to be added to the re-dispersion solution. The titanium oxide photocatalyst of Reference Example 2 had a specific surface area of 251 $m^2/g$ (determined by the BET method), and the amount of eluted F thereof was 5 wt %. That is, 95 wt % of fluorine in the titanium oxide photocatalyst was bonded chemically to the anatase-type titanium oxide. It should be noted that in the preparation of the titanium oxide photocatalyst of Reference Example 2, a part of the re-dispersion solution was dried at 50° C. under a reduced pressure so as to be powdered and the amount of n-butylamine adsorbed by the obtained powder was measured by the aforementioned measuring method. The amount was found to be 3 µmol/g.

Reference Example 3

A titanium oxide photocatalyst of Reference Example 3 was obtained in the same manner as in Reference Example 1 described above, except that hydrofluoric acid (manufactured by Wako Pure Chemical Industries, Ltd., guaranteed reagent) equivalent to 10 wt % in terms of fluorine (element) was used as a hydrofluoric acid to be added to the re-dispersion solution. The titanium oxide photocatalyst of Reference Example 3 had a specific surface area of 260 m$^2$/g (determined by the BET method), and the amount of eluted F thereof was 5 wt %. That is, 95 wt % of fluorine in the titanium oxide photocatalyst was chemically bonded to the anatase-type titanium oxide. It should be noted that in the preparation of the titanium oxide photocatalyst of Reference Example 3, a part of the re-dispersion solution was dried at 50° C. under a reduced pressure so as to be powdered and the amount of n-butylamine adsorbed by the obtained powder was measured by the aforementioned measuring method. The amount was found to be 1 μmol/g.

Reference Example 4

A titanium oxide photocatalyst of Reference Example 4 was obtained in the same manner as in Reference Example 1 described above, except that the temperature for the thermal hydrolysis of titanyl sulfate was set at 85° C. The titanium oxide photocatalyst of Reference Example 4 had a specific surface area of 340 m$^2$/g (determined by the BET method). It should be noted that in the preparation of the titanium oxide photocatalyst of Reference Example 4, a part of the re-dispersion solution was dried at 50° C. under a reduced pressure so as to be powdered and the amount of n-butylamine adsorbed by the obtained powder was measured by the aforementioned measuring method. The amount was found to be 7 μmol/g.

Reference Example 5

A titanium oxide photocatalyst of Reference Example 5 was obtained in the same manner as in Reference Example 1 described above, except that the re-dispersion solution prepared was held in an autoclave at 100° C. for 5 hours and thereafter hydrofluoric acid was added to the re-dispersion solution. The titanium oxide photocatalyst of Reference Example 5 had a specific surface area of 205 m$^2$/g (determined by the BET method). It should be noted that in the preparation of the titanium oxide photocatalyst of Reference Example 5, a part of the re-dispersion solution after it was held at 100° C. for 5 hours was dried at 50° C. under a reduced pressure so as to be powdered and the amount of n-butylamine adsorbed by the obtained powder was measured by the aforementioned measuring method. The amount was found to be 8 μmol/g.

Reference Example 6

A titanium oxide photocatalyst of Reference Example 6 was obtained in the same manner as in Reference Example 1 described above, except that ammonium fluoride (manufactured by Wako Pure Chemical Industries, Ltd., guaranteed reagent) equivalent to 5.0 wt % in terms of fluorine (element) was added in place of hydrofluoric acid and that, after the addition of ammonium fluoride, a reaction was allowed to occur with the pH being maintained at 1 using hydrochloric acid. The titanium oxide photocatalyst of Reference Example 6 had a specific surface area of 270 m$^2$/g (determined by the BET method). It should be noted that in the preparation of the titanium oxide photocatalyst of Reference Example 6, a part of the re-dispersion solution was dried at 50° C. under a reduced pressure so as to be powdered and the amount of n-butylamine adsorbed by the obtained powder was measured by the aforementioned measuring method. The amount was found to be 4 μmol/g.

Reference Example 7

A titanium oxide photocatalyst of Reference Example 7 was obtained in the same manner as in Reference Example 1 described above, except that sodium fluoride (manufactured by Wako Pure Chemical Industries, Ltd., guaranteed reagent) equivalent to 5.0 wt % in terms of fluorine (element) was added in place of hydrofluoric acid and that, after the addition of sodium fluoride, a reaction was allowed to occur with the pH being maintained at 1 using hydrochloric acid. The titanium oxide photocatalyst of Reference Example 7 had a specific surface area of 268 m$^2$/g (determined by the BET method). It should be noted that in the preparation of the titanium oxide photocatalyst of Reference Example 7, a part of the re-dispersion solution was dried at 50° C. under a reduced pressure so as to be powdered and the amount of n-butylamine adsorbed by the obtained powder was measured by the aforementioned measuring method. The amount was found to be 5 μmol/g.

Reference Example 8

A titanium oxide photocatalyst of Reference Example 8 was obtained in the same manner as in Reference Example 1 described above, except that sodium fluoride (manufactured by Wako Pure Chemical Industries, Ltd., guaranteed reagent) equivalent to 5.0 wt % in terms of fluorine (element) was added in place of hydrofluoric acid and that, after the addition of sodium fluoride, a reaction was allowed to occur with the pH being maintained at 3 using hydrochloric add. The titanium oxide photocatalyst of Reference Example 8 had a specific surface area of 272 m$^2$/g (determined by the BET method). It should be noted that in the preparation of the titanium oxide photocatalyst of Reference Example 8, a part of the re-dispersion solution was dried at 50° C. under a reduced pressure so as to be powdered and the amount of n-butylamine adsorbed by the obtained powder was measured by the aforementioned measuring method. The amount was found to be 5 μmol/g.

Comparative Example 1

A titanium oxide photocatalyst of Comparative Example 1 was obtained in the same manner as in Reference Example 1 described above, except that a hydrofluoric acid (manufactured by Wako Pure Chemical Industries, Ltd., guaranteed reagent) equivalent to 4 wt % in terms of fluorine (element) was used as hydrofluoric acid to be added to the re-dispersion solution. The titanium oxide photocatalyst of Comparative Example 1 had a specific surface area of 268 m$^2$/g (determined by the BET method). It should be noted that in the preparation of the titanium oxide photocatalyst of Comparative Example 1, a part of the re-dispersion solution was dried at 50° C. under a reduced pressure so as to be powdered and the amount of n-butylamine adsorbed by the obtained powder was measured by the aforementioned measuring method. The amount was found to be 6 μmol/g.

Comparative Example 2

A titanium oxide photocatalyst of Comparative Example 2 was obtained in the same manner as in Reference Example 1 described above, except that when the substance obtained by filtration was washed with water and a cake was obtained, the water washing was performed until the electric conductivity of the washing liquid became 1 mS/cm. The titanium oxide photocatalyst of Comparative Example 2 had a specific surface area of 276 m$^2$/g (determined by the BET method). It should be noted that in the preparation of the titanium oxide photocatalyst of Comparative Example 2, a part of the re-dispersion solution was dried at 50° C. under a reduced pressure so as to be powdered and the amount of n-butylamine adsorbed by the obtained powder was measured by the aforementioned measuring method. The amount was found to be 6 μmol/g.

Comparative Example 3

A titanium oxide photocatalyst of Comparative Example 3 was obtained in the same manner as in Reference Example 1 described above, except that when the pH of the obtained shiny aqueous solution was adjusted, the adjustment was carried out icing sodium hydroxide, and that when the obtained reaction product was washed with water, the water washing was performed until the electric conductivity of the washing liquid became 400 μS/cm. The titanium oxide photocatalyst of Comparative Example 3 had a specific surface area of 255 m$^2$/g (determined by the BET method). It should be noted that in the preparation of the titanium oxide photocatalyst of Comparative Example 3, a part of the re-dispersion solution was dried at 50° C. under a reduced pressure so as to be powdered and the amount of n-butylamine adsorbed by the obtained powder was measured by the aforementioned measuring method. The amount was found to be 30 μmol/g.

Comparative Example 4

A titanium oxide photocatalyst of Comparative Example 4 was obtained in the same manner as in Reference Example 1 described above, except that when the pH of the obtained slurry aqueous solution was adjusted, the adjustment was carried out using ammonia water until the pH became 7.0. The titanium oxide photocatalyst of Comparative Example 4 had a specific surface area of 271 m$^2$/g (determined by the BET method). It should be noted that in the preparation of the titanium oxide photocatalyst of Comparative Example 4, a part of the redispersion solution was dried at 50° C. under a reduced pressure so as to be powdered and the amount of n-butylamine adsorbed by the obtained powder was measured by the aforementioned measuring method. The amount was found to be 13 μmol/g.

Comparative Example 5

After the re-dispersion solution was prepared in the same manner as in Reference Example 1 described above, sodium fluoride (manufactured by Wako Pure Chemical Industries, Ltd., guaranteed reagent) equivalent to 5.0 wt % in terms of fluorine (element) with respect to titanium oxide was added to this re-dispersion solution, and a reaction was allowed to occur at 25° C. for 60 minutes with the pH thereof being maintained at 1. Thereafter, without the obtained reaction product being washed with water, the total amount of the dispersion solution was dried and solidified by evaporation in air at 130° C. for 10 hours so as to be powdered, whereby a titanium oxide photocatalyst of Comparative Example 5 was obtained. The titanium oxide photocatalyst of Comparative Example 5 had a specific surface area of 269 m$^2$/g (determined by the BET method), and the amount of eluted F thereof was 50 wt %. That is, the proportion of fluorine chemically bonded to the anatase-type titanium oxide was 50 wt %. It should be noted that in the preparation of the titanium oxide photocatalyst of Comparative Example 5, a part of the re-dispersion solution was dried at 50° C. under a reduced pressure so as to be powdered and the amount of n-butylamine adsorbed by the obtained powder was measured by the aforementioned measuring method. The amount was found to be 4 μmol/g.

Comparative Example 6

A titanium oxide photocatalyst of Comparative Example 6 was obtained in the same manner as in Reference Example 1 described above, except that the re-dispersion solution prepared was held in an autoclave at 130° C. for 1 hour so that a hydrothermal reaction occurred, and thereafter hydrofluoric acid was added thereto. The titanium oxide photocatalyst of Comparative Example 6 had a specific surface area of 185 m$^2$/g (determined by the BET method). It should be noted that in the preparation of the titanium oxide photocatalyst of Comparative Example 6, a part of the re-dispersion solution after it was held at 130° C. for 1 hour was dried at 50° C. under a reduced pressure so as to be powdered and the amount of n-butylamine adsorbed by the obtained powder was measured by the aforementioned measuring method. The amount was found to be 5 μmol/g.

Comparative Example 7

A solution of titanyl sulfate (manufactured by SAKAI Chemical Industry Co., Ltd.) in which the concentration as to titanium oxide was 100 g/L and the concentration as to sulfuric add was 250 g/L was kept at 100° C. for 3 hours to be hydrolyzed thermally. The pH of the obtained slurry aqueous solution was adjusted with ammonia water until the pH became 8.0, and was filtered. Then, the substance obtained by filtration was washed thoroughly with water to remove salts as impurities. Here, the water washing was performed until the electric conductivity of the washing liquid became 200 μS/cm. The cake obtained was dried in air at 130° C. for 5 hours so as to be powdered, whereby a titanium oxide photocatalyst of Comparative Example 7 was obtained. The titanium oxide photocatalyst of Comparative Example 7 had a specific surface area of 274 m$^2$/g (determined by the BET method), and the amount of eluted F was found to be 0 wt %. It should be noted that in the preparation of the titanium oxide photocatalyst of Comparative Example 7, a part of the cake obtained was dried at 50° C. under a reduced pressure so as to be powdered, and the amount of n-butylamine adsorbed by the obtained powder was measured by the aforementioned measuring method. The amount was found to be 2 μmol/g.

Comparative Example 8

To 20 g of titanium hydroxide (principal component: β-titanium acid, manufactured by SAKAI Chemical Industry Co., Ltd.), 50 g of a 0.15 wt % aqueous ammonium fluoride solution was added and dried, whereby a mixture was obtained. 3.2 g of the obtained mixture was fed into an electric furnace (energy-saving temperature-rising electric furnace manufactured by MOTOYAMA, trade name: RH-2025D), and the temperature was increased from room temperature to 350° C. in air for 105 minutes. After it was maintained in this state for 1 hour so as to be calcined, it was cooled gradually, whereby 2.9 g of titanium oxide was obtained as a titanium oxide photocatalyst of Comparative Example 8. The titanium oxide photocatalyst of Comparative Example 8 had a specific surface area of 44 m²/g (determined by the BET method), and the amount of eluted F thereof was 25 wt %. It should be noted that in the preparation of the titanium oxide photocatalyst of Comparative Example 8, a part of the cake obtained was dried at 50° C. under a reduced pressure so as to be powdered, and the amount of n-butylamine adsorbed by the obtained powder was measured by the aforementioned measuring method. The amount was found to be 8 µmol/g.

Analysis of Physical Properties

As to each of the titanium oxide photocatalysts of Reference Examples 1 to 8 and Comparative Examples 1 to 8, the content of fluorine and the content of sodium were determined. The content of fluorine was analyzed by absorptiometry (JIS K0102), and the content of fluorine in the photocatalyst was determined by percentage by weight. Further, the content of sodium was analyzed by inductively coupled high-frequency plasma spectrometry (ICP spectrometry), and the content of sodium in the photocatalyst was determined as ppm by weight. Further, in the preparation of each titanium oxide photocatalyst, a part of the re-dispersion solution obtained (a part of the cake in the case of Comparative Example 7) was dried at 50° C. under a reduced pressure so as to be powdered. The content of sodium in the powder was analyzed by ICP spectrometry, and the content of sodium in the starting material was determined as ppm by weight. Further, as to each of the titanium oxide photocatalysts of Reference Examples 1 and 2 and Comparative Examples 1, 2, 4, and 7, the ratio by weight of fluorine on surfaces of the photocatalyst with respect to titanium on the surfaces of the photocatalyst (hereinafter this ratio is referred to as "surface F ratio") was determined by a method described below. The results of the same are shown in Table 1. It should be noted that, as shown in Table 1, the contents of sodium of Reference Examples 1 to 3, 6 to 8 and Comparative Examples 1 and 5 were different even though the re-dispersion solutions thereof were prepared in the same way. As to the reason for this, it is considered that the difference was caused by variations in lots of titanyl sulfate as a raw material, and analytical errors. Further, the titanium oxide photocatalysts in Reference Examples 1 to 8 were analyzed by a photoelectron spectroscopic analyzer, and every photocatalyst showed a spectrum in which a peak top of $F_{1s}$ appeared in a range of 683 eV to 686 eV.

Monument of Electric Conductivity

The electric conductivity of water (25° C.) collected after washing was measured with a pH/cond meter (manufactured by HORIBA, Ltd, D-54 (trade name)).

Determination of Anatase Type

Each of the titanium oxide photocatalysts obtained in Reference Examples 1 to 8 was analyzed with a powder X-ray diffractometer (working electrode: copper electrode), and a diffraction peak appeared at a diffraction angle $2\theta=25.5°$. This means that every titanium oxide photocatalyst obtained in Reference Examples 1 to 8 was determined to be an anatase type.

Measurement of Amount of Eluted Fluorine 0.1 g of titanium oxide obtained in Reference Example or Comparative Example was suspended in 100 ml of pure water, and after irradiated with ultrasonic waves for 15 minutes, it was centrifuged. The supernatant fluid obtained was subjected to colorimetric analysis using PACKTEST (registered trade name) manufactured by Kyoritsu Chemical Check Lab, Corp., and an amount of eluted fluorine ions were determined. Based on this amount of eluted fluorine, the amount of fluorine chemically bonded to titanium oxide can be determined.

Method for Measurement of Surface F Ratio

As to each of the titanium oxide photocatalyst powders, 1 g of the same was weighed, placed in a 10-mm-diameter molding die, and was pressed by stamping in a manner such that a load of 1 t/cm² was applied to each piece, so as to be formed into a 10-mm-diameter pellet. Then, this molded pellet was broken so that a small fraction having a flat surface was produced, and this fraction was fixed on a sample stage with a double-faced tape, as a sample to be subjected to photoelectron spectroscopy. This sample was left in vacuum for one day, and thereafter photoelectron spectra emitted from the 2p orbital of titanium (Ti), the 1s orbital of fluorine (F), and the 1s orbital of carbon (C) were measured with a photoelectron spectroscope (ESCA-850 model manufactured by Shimadzu Corporation, source of X-rays: MgKα) under the conditions of 8 kV and 30 mA. Then, with a value of the same emitted from the 1s orbital of C thus determined being compensated to be 284.8 eV, energies of the spectra determined by the measurement at the 2p orbital of Ti and the 1s orbital of F were compensated accordingly. With bonding energies of the spectrum being set to the corrected values, respectively, a value determined by the following calculation formula is assumed to be the surface F ratio:

$$\text{Surface } F \text{ ratio}=N_F \times 19.0/(N_{Ti} \times 47.9)$$

where $N_F$ represents the number of atoms of F determined from a spectral area of the 1s orbital of F, $N_{Ti}$ represents the number of atoms of Ti determined from a spectral area of the 2p orbital of Ti.

Evaluation of Photocatalytic Activity

Using the respective titanium oxide photocatalysts of Reference Examples 1 to 8 and Comparative Examples 1 to 8, air purification devices as shown in FIG. 4 were assembled, and the photocatalytic activities were evaluated. Acetaldehyde was used as an odorous component. The configuration of the photocatalytic member and the evaluation method are described below.

Configuration of Photocatalytic Member

As the photocatalytic member 21, a photocatalytic member was prepared that included a 12 cm×10 cm substrate 21a made of glass and a photocatalyst layer 21b that was formed on the substrate 21a so as to have a size of 12 cm×6.4 cm (thickness: 3 µm). It should be noted that the photocatalyst layer 21b was formed in the following manner: 5 g of each of the powders made of the titanium oxide photocatalysts of Reference Examples 1 to 8 and Comparative Examples 1 to 8 was dispersed in ethanol so as to become a paste, and the paste was applied over the substrate 21a, and was left at room temperature for one hour so that most of ethanol evaporated.

Evaluation Method Using Air Purification Device

Before the photocatalytic member 21 was placed in the container 20, the photocatalyst layer 21b was irradiated with ultraviolet rays having an intensity of 5 mW/cm² using the light sources 22 (center wavelength: 352 nm, UV lamps manufactured by Toshiba Lighting & Technology Corporation) for 240 minutes, whereby organic substances adhering to the surface of the photocatalyst layer 21a were decomposed completely. This photocatalytic member 21 was then left to stand in the container 20 (capacity: 16 L). The container 20 was filled with acetaldehyde so that the concentration of the acetaldehyde gas in the container became 500 mol ppm, and was sealed. After this was left to stand for 60 minutes without ultraviolet rays irradiation over the photocatalyst layer 21b and an adsorption equilibrium was reached, a change in the concentration of the acetaldehyde in the container 20 and an amount of generated carbon dioxide were analyzed by gas chromatography while the photocatalyst layer 21b was irradiated with ultraviolet rays having an intensity of 21 mW/cm² using the light sources 22. The superiorities and inferiorities of the respective titanium oxide photocatalysts were evaluated based on the carbon dioxide generation rates thus determined. The results are shown in Table 1.

Evaluation Method Using Liquid Purification Device

After a solution obtained by adding 1 mg of methylene blue into 200 mL of pure water was fed into the Petri dish 80, the photocatalyst layer 71b was irradiated with ultraviolet rays having an intensity of 1 mW/cm² using the black light 72 (center wavelength: 352 nm, UV lamp manufactured by

TABLE 1

|  | Physical property of starting material | | Physical property of titanium oxide photocatalyst | | | | | |
|---|---|---|---|---|---|---|---|---|
|  | n-butylamine adsorption amount (μmol/g) | Na content (wt ppm) | F content (wt %) | Na content (wt ppm) | Na content/ F content | Surface F ratio | Proportion of chemically bonded fluorine (wt %) | Carbon dioxide generation rate (mol ppm/hour) |
| Ref Ex. 1 | 2 | 802 | 2.9 | 229 | 0.0079 | 0.1 | 95 | 745 |
| Ref. Ex. 2 | 3 | 634 | 3.1 | 120 | 0.0039 | 0.13 | 95 | 772 |
| Ref. Ex. 3 | 1 | 440 | 3.4 | 5 | 0.0002 | — | 95 | 818 |
| Ref Ex. 4 | 7 | 824 | 3 | 290 | 0.0097 | — | — | 650 |
| Ref Ex. 5 | 8 | 770 | 2.7 | 201 | 0.0074 | — | — | 670 |
| Ref. Ex. 6 | 4 | 806 | 2.5 | 230 | 00092 | — | — | 693 |
| Ref Ex. 7 | 5 | 802 | 2.8 | 270 | 0.0096 | — | — | 689 |
| Ref. Ex. 8 | 5 | 815 | 2.5 | 293 | 0.0117 | — | — | 606 |
| Comp. Ex 1 | 6 | 812 | 2.3 | 200 | 0.0087 | 0.07 | — | 540 |
| Comp. Ex. 2 | 6 | 1150 | 2.3 | 300 | 0.013 | 0.07 | — | 509 |
| Comp. Ex 3 | 30 | 4760 | 1.6 | 980 | 0.0613 | — | — | 520 |
| Comp. Ex 4 | 13 | 957 | 2.2 | 250 | 0.0114 | 0.07 | — | 571 |
| Comp. Ex. 5 | 4 | 813 | 5 | 60000 | 1.2 | — | 50 | 300 |
| Comp Ex 6 | 5 | 816 | 2.1 | 199 | 0.0095 | — | — | 387 |
| Comp. Ex. 7 | 2 | 827 | 0 | 810 | — | 0 | 0 | 321 |
| Comp Ex 8 | 8 | 77 | 1.5 | 9 | 0.0006 | — | 75 | 275 |

Table 1 shows that all the titanium oxide photocatalysts of Reference Examples 1 to 8, in which the content of fluorine was 2.5 wt % to 3.5 wt %, exhibited faster carbon dioxide generation rates (acetaldehyde decomposition rates) and superior photocatalytic activity compared to those of Comparative Examples 1 to 8, in which the content of fluorine was out of the foregoing range. Besides, as shown in Table 1, the n-butylamine adsorption amounts of the titanium oxide photocatalysts of Reference Examples 3 to 3, 6 to 8 and Comparative Examples 1 and 5 were different even though the re-dispersion solutions thereof were prepared in the same way. It is considered that the difference was caused by variations in lots of titanyl sulfate as a raw material, and analytical errors.

Evaluation of Photocatalytic Activity 2

Figure 10:
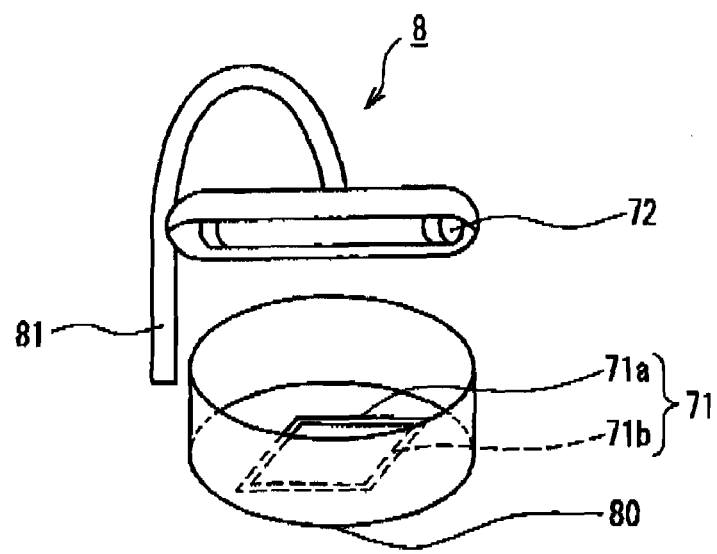
FIG. 10 is a perspective view of a liquid purification device used in the evaluation of photocatalytic activity.

Using the titanium oxide photocatalysts of Reference Examples 1 and 2 and Comparative Examples 1 and 7, photocatalytic members were produced, and using these photocatalytic members, liquid purification devices shown in FIG. 10 were assembled. Using each of these liquid purification devices, photocatalytic activity thereof was evaluated. Methylene blue, which is a pigment, was used as the liquid-form organic substance, and a degree of discoloration of methylene blue with time was measured. The configuration of the liquid purification device and the evaluation method are described below.

Configuration of Liquid Purification Device

FIG. 10 is a perspective view of a liquid purification device used in the evaluation of photocatalytic activity. As shown in FIG. 10, the liquid purification device 8 includes a Petri dish 80, a photocatalytic member 71 disposed in the Petri dish 80, a black light 72 that was disposed so as to face the photocatalytic member 71, and a stand 81 for fixing the black light 72. The photocatalytic member 71 was produced in the same manner as the method of producing the photocatalytic member used in the above-described evaluation method using the air purification device.

Toshiba Lighting & Technology Corporation), without light entering from the outside. Then, from the start of the irradiation until 4 hours later, 5 mL of the foregoing solution was sampled every one hour. Each sample was centrifuged using a centrifuge at 3000 rpm for 15 minutes, and a supernatant fluid was sampled. Then, the supernatant fluid thus sampled was placed in a quartz cell, and an absorbance thereof was measured using a spectrophotometer (manufactured by JASCO Corporation, V-570 model). It should be noted that since a phenomenon in which the wavelength of absorbed light shifted as the decomposition of methylene blue proceeded was observed, the absorbance at the top point (peak position) of the curve was assumed to be the absorbance of the sample. Then, an absorbance of an aqueous methylene blue solution prepared at a different concentration preliminarily (standard fluid) was measured so that a calibration curve was produced, and a concentration (mg/L) of the methylene blue renal fling in the solution was determined based on the foregoing calibration curve and the absorbance of the supernatant fluid measured by the aforementioned method. The results are shown in FIG. 11.

Figure 11:
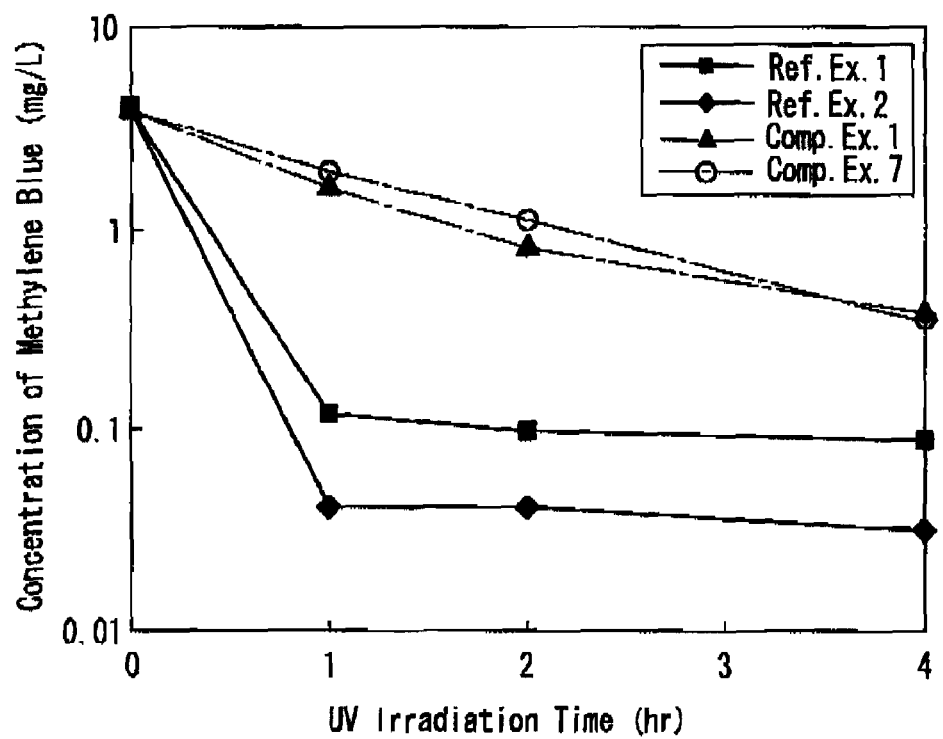
FIG. 11 is a graph showing the relationship between the UV irradiation time and the concentration of methylene blue in each of Reference Examples 1 and 2 and Comparative Examples 1 and 7.

As is clear from FIG. 11, in the cases of the titanium oxide photocatalysts of Reference Examples 1 and 2, significantly higher rates of discoloration (decomposition of methylene blue) were observed, as compared with the cases of Comparative Examples 1 and 7, which means that the titanium oxide photocatalysts of Reference Examples 1 and 2 exhibited excellent photocatalytic activity.

Examples 1 to 10

As Examples 1 to 10, photocatalytic materials were prepared by physically mixing the titanium oxide photocatalyst of Reference Example 3 described above and zeolite for about 5 minutes using a mortar. Zeolite used for Examples 1 to 9 was HSZ-890HOA, ZSM-5 form (silica/alumina ratio=1890) manufactured by Mach Corporation, and zeolite used for Example 10 was HSZ-690HOA, mordenite form (silica/alumina ratio=240) manufactured by Tosoh Corporation. It should be noted that the content of zeolite in each photocatalytic material was as shown in Table 2. As the titanium oxide photocatalyst of Comparative Example 9, SSP-25 manufactured by SAKAI Chemical Industry Co., Ltd. was prepared.

Evaluation of Photocatalytic Activity 3

Photocatalytic materials were produced from materials obtained in Examples 1 to 10, Reference Example 3, and Comparative Example 9, air purification devices shown in FIG. 4 were assembled using these, and photocatalytic activity was evaluated in the same manner as described above. The results are shown in Table 2. It should be noted that Table 2 shows ratios of carbon dioxide generation rates of Examples 1 to 10 and Reference Example 3 with respect to the carbon dioxide generation rate of Comparative Example 9, which is assumed to be 1.0.

TABLE 2

| | Titanium oxide Fluorine content (wt %) | Zeolite Content (wt %) | Zeolite Trade name | Evaluation of photocatalytic activity Ratio of carbon dioxide generation rate | Evaluation of photocatalytic activity Generation rate (mol ppm/hr) |
|---|---|---|---|---|---|
| Ex. 1 | 3.4 | 10 | HSZ-890HOA | 3.8 | 1151 |
| Ex. 2 | 3.4 | 20 | HSZ-890HOA | 5.5 | 1666 |
| Ex. 3 | 3.4 | 30 | HSZ-890HOA | 6.2 | 1878 |
| Ex. 4 | 3.4 | 40 | HSZ-890HOA | 6.0 | 1818 |
| Ex. 5 | 3.4 | 50 | HSZ-890HOA | 5.5 | 1666 |
| Ex. 6 | 3.4 | 60 | HSZ-890HOA | 4.6 | 1394 |
| Ex. 7 | 3.4 | 70 | HSZ-890HOA | 4.0 | 1212 |
| Ex. 8 | 3.4 | 80 | HSZ-890HOA | 3.8 | 1151 |
| Ex. 9 | 3.4 | 90 | HSZ-890HOA | 3.6 | 1091 |
| Ex. 10 | 3.4 | 30 | HSZ-690HOA | 5.9 | 1787 |
| Ref. Ex. 3 | 3.4 | 0 | — | 2.7 | 818 |
| Comp. Ex. 9 | 0 | 0 | — | 1.0 | 303 |

As is clear from Table 2, each of the photocatalytic members of Example 1 to 10 exhibited a faster carbon dioxide generation rate (acetaldehyde decomposition rate) as compared with Reference Example 3 and Comparative Example 9, i.e., superior photocatalytic activity. It should be noted that in Examples 1 to 10, HSZ-890HOA or HSZ-690HOA manufactured by Tosoh Corporation was used as zeolite, but the present invention is not limited to this configuration. The same effect can be achieved in the case where, for example, ABSCENTS™-1000 manufactured by Union Showa K.K., ABSCENTS™-2000 manufactured by Union Showa K.K., Smellrite™ manufactured by Union Showa K.K., or the like is used.

Examples 11 to 18

Each of photocatalytic materials of Examples 11 to 18 shown in Table 3 below was prepared by physically mixing the titanium oxide photocatalyst of Reference Example 3 or 6 and zeolite for about 5 minutes using a mortar. Using the photocatalytic materials of Examples 11 to 18, photocatalytic members were produced in the same manner as in Examples 1 to 10, and photocatalytic activity thereof was evaluated. The results are shown in Table 3 below, together with the trade names of zeolite used, and the contents of zeolite in the photocatalytic materials. Ratios of carbon dioxide generation rates shown in Table 3 are ratios of the rates with respect to the carbon dioxide generation rate of Comparative Example 9, which is assumed to be 1.0.

TABLE 3

| | Titanium oxide Fluorine content (wt %) | Zeolite Content (wt %) | Zeolite Trade name | Evaluation of photocatalytic activity Ratio of carbon dioxide generation rate | Evaluation of photocatalytic activity Generation rate (mol ppm/hr) |
|---|---|---|---|---|---|
| Ex. 11 | 2.5 | 30 | HSZ-890HOA | 4.5 | 1368 |
| Ex. 12 | 2.5 | 60 | HSZ-890HOA | 3.8 | 1151 |
| Ex. 13 | 2.5 | 90 | HSZ-890HOA | 3.5 | 1060 |
| Ex. 14 | 3.4 | 30 | ABSCENTS-1000 | 5.8 | 1757 |
| Ex. 15 | 3.4 | 30 | ABSCENTS-2000 | 6.0 | 1818 |
| Ex. 16 | 3.4 | 30 | Smellrite | 6.0 | 1818 |
| Ex. 17 | 3.4 | 30 | HiSiv-3000 | 5.9 | 1789 |
| Ex. 18 | 3.4 | 30 | HiSiv-3000 (50 wt %) HSZ-890HOA (50 wt %) | 6.1 | 1836 |

As is clear from Table 3, each Example exhibited a carbon dioxide generation rate (acetaldehyde decomposition rate) of more than 1000 mol ppm/hour, which means each Example exhibited superior photocatalytic activity.

Example 19

A punched aluminum plate whose surfaces had been anodized (aperture ratio: 35.4%, 20 cm×10 cm, thickness: 1 mm) was prepared as a substrate. The photocatalytic material of Example 3 (5 g) was dispersed in 10 ml of ethanol so that a paste was obtained. This paste-form photocatalytic material was applied over the substrate (18 cm×8 cm) and was left to stand at room temperature for one hour. Thereafter, it was dried at 80° C. for 6 hours in a drier, whereby a photocatalyst layer (thickness: about 70 μm) was formed. In the obtained photocatalyst layer, about 1 g of the photocatalytic material was fixed. The obtained photocatalyst layer was irradiated with ultraviolet rays having an intensity of 5 mW/cm$^2$ (center wavelength: 352 nm, black-light-blue lamp under the brand name of "National") for 2 hours so that organic substances adhering to a surface of the photocatalyst layer were decomposed. Thus, a photocatalytic member in a filter form was produced.

Example 20

A photocatalytic member was produced in the same manner as in Example 19 except that the photocatalytic material of Example 9 was used as the photocatalytic material.

Example 21

A photocatalytic member was produced in the same manner as in Example 19 except that the photocatalytic material of Example 1 was used as the photocatalytic material.

Example 22

A photocatalytic member was produced in the same manner as in Example 19 except that the photocatalytic material of Example 16 was used as the photocatalytic material.

Comparative Example 10

Active carbon (GA crushed carbon, manufactured by Cataler Corporation) was dispersed in 10 ml of ethanol so that a paste was obtained. This paste-form photocatalytic material was applied over the same substrate as that in Example 19 (18 cm×8 cm) and was left to stand at room temperature for one hour. Thereafter, it was dried at 80° C. for 6 hours in a drier, whereby a filter was produced. The obtained filter was in such a state that granular active carbon was deposited on the substrate, and a thickness of the active carbon layer could not be determined. The active carbon contained in the active carbon layer was about 1 g (weight in a dried state).

Comparative Example 11

Titanium oxide (trade name: P25, Nippon Aerosil Co., Ltd., anatase-type titanium oxide: 80%, rutile-type titanium oxide: 20%) not containing fluorine and zeolite (HSZ-890HOA, manufactured by Tosoh Corporation) were mixed physically for about 5 minutes with a mortar, so that a photocatalytic material was prepared. A photocatalytic member was produced in the same manner as in Example 19 except that the foregoing photocatalytic material was used as the photocatalytic material.

Comparative Example 12

The titanium oxide photocatalyst of Reference Example 3 and zeolite (HSZ-390HUA, manufactured by Tosoh Corporation, Y-form zeolite, silica/alumina ratio (molar component ratio: 400)) were mixed physically for about 5 minutes with a mortar, so that a photocatalytic material was prepared. A photocatalytic member was produced in the same manner as in Example 19 except that the foregoing photocatalytic material was used as the photocatalytic material.

Evaluation of Filter Recycling

Each of the photocatalytic members of Examples 19 to 22 and Comparative Examples 11 and 12 and the filter of Comparative Example 10 were disposed on the parting plate 25a of the cross-flow air purification device (capacity: 100 L) shown in FIG. 5. The device 201 was filled with acetaldehyde so that the concentration of acetaldehyde in the device 201 became 10 mol ppm, and was sealed. After this, it was left to stand for 60 minutes without ultraviolet rays irradiation over the photocatalyst layer 21b. After it was checked and seen that an adsorption equilibrium was reached, the photocatalyst layer 21b was irradiated with ultraviolet rays having an intensity of 1 mW/cm$^2$ with the light source 22 (center wavelength: 352 nm, black-light-blue lamp under the brand name of "National") for 2 hours, whereby aldehyde adhering to the titanium oxide photocatalyst and zeolite was decomposed and removed. The concentration of acetaldehyde after the decomposition and removal was analyzed with a gas chromatograph. The device 201 again was filled with acetaldehyde so that the concentration of acetaldehyde became 10 mol ppm. Then, 5 cycles of the leaving of the same to stand for 60 minutes, the irradiation with ultraviolet rays, the analysis, and the refilling were carried out. The ratio of deodorization (deodorization ratio) and the ratio of decrease in adsorbability (adsorbability decrease ratio) were calculated using the determined concentrations of acetaldehyde. The determined ratios of decrease in adsorbability are shown in Table 4 below.

$$\text{Deodorization ratio (\%)} = \frac{(\text{initial concentration} - \text{concentration of remunants})}{\text{initial concentration}} \times 100$$

Adsorbability decrease ratio=(deodorization ratio after 1 cycle)−(deodorization ratio after 5 cycles)

TABLE 4

| | Titanium oxide Fluorine content (wt %) | Zeolite Content (wt %) | Zeolite Trade name | Adsorption decrease ratio |
|---|---|---|---|---|
| Ex. 19 | 3.4 | 30 | HSZ-890HOA | None |
| Ex. 20 | 3.4 | 90 | HSZ-890HOA | None |
| Ex. 21 | 3.4 | 10 | HSZ-890HOA | 1% or less |
| Ex. 22 | 3.4 | 30 | Smellrite | 1% or less |
| Comp. Ex. 10 | 3.4 | 0 | Active carbon | 78% |
| Comp. Ex. 11 | 0 | 30 | — | 10% |
| Comp. Ex. 12 | 3.4 | 30 | HSZ-390HUA | 8% |

All of the photocatalytic members of Examples 19 to 22 maintained high adsorbability, with substantially no decrease in adsorbability even after 5 cycles of adsorption and decomposition. Besides, it was proved that when the photocatalytic members of Examples 19 to 22 were irradiated with ultraviolet rays of 1 mW/cm$^2$ for 2 hours, their ability of adsorbing and decomposing acetaldehyde could be recovered (the photocatalytic members could be recycled).

INDUSTRIAL APPLICABILITY

The present invention is useful for a purification device used for the purpose of, for example, deodorization, odor elimination, air purification, and liquid purification.

The invention claimed is:

1. A photocatalytic material consisting essentially of a titanium oxide photocatalyst and zeolite, the titanium oxide photocatalyst containing at least an anatase-type titanium oxide and fluorine,
    wherein a content of the fluorine in the titanium oxide photocatalyst is 2.5 wt % to 3.5 wt %,
    90 wt % or more of the fluorine is bonded chemically to the anatase-type titanium oxide, and
    when a content of sodium in the titanium oxide photocatalyst is assumed to be A wt % and a content of the fluorine in the titanium oxide photocatalyst is assumed to B wt %, a ratio A/B is 0.01 or less.

2. The photocatalytic material according to claim 1, wherein the zeolite contains at least one of a mordenite-form zeolite and a ZSM-5-form zeolite.

3. The photocatalytic material according to claim 1,
    wherein the zeolite contains silica and alumina, and
    a molar component ratio between the silica and the alumina (silica/alumina) in the zeolite is 240 or more.

4. The photocatalytic material according to claim 1, wherein 100 wt % of the fluorine is bonded chemically to the anatase-type titanium oxide.

5. The photocatalytic material according to claim 1, wherein the chemical bonding is ionic bonding.

6. The photocatalytic material according to claim 1, wherein at least a part of the fluorine chemically bonded to the anatase-type titanium oxide is located on a surface of the anatase-type titanium oxide.

7. The photocatalytic material according to claim 1, wherein a content of the zeolite in the photocatalytic material is 10 wt % or more.

8. A photocatalytic member comprising a substrate and photocatalyst layer formed on a surface of the substrate,
    wherein the photocatalyst layer contains the photocatalytic material according to claim 1.

9. The photocatalytic member according to claim 8, wherein the substrate is a substrate having air permeability.

10. A purification device comprising:
    the photocatalytic member according to claim 8; and
    a light source that irradiates the photocatalytic member with light having a wavelength of 400 nm or less.

11. The purification device according to claim 10, further comprising blowing means that introduces a gas containing organic substances toward the photocatalytic member.

* * * * *